US011466265B2

(12) United States Patent
Younger et al.

(10) Patent No.: US 11,466,265 B2
(45) Date of Patent: Oct. 11, 2022

(54) HIGH-THROUGHPUT SCREENING METHODS TO IDENTIFY SMALL MOLECULE TARGETS

(71) Applicant: A-Alpha Bio, Inc., Seattle, WA (US)

(72) Inventors: David Younger, Seattle, WA (US); Randolph Lopez, Seattle, WA (US); Arpita Sen, Seattle, WA (US); Ryan Emerson, Seattle, WA (US)

(73) Assignee: A-ALPHA BIO, INC., Seattle, WA (US)

(*) Notice: Subject to any disclaimer, the term of this patent is extended or adjusted under 35 U.S.C. 154(b) by 0 days.

(21) Appl. No.: 17/516,237

(22) Filed: Nov. 1, 2021

(65) Prior Publication Data
US 2022/0090052 A1 Mar. 24, 2022

(51) Int. Cl.
C12N 15/10 (2006.01)
C12N 1/16 (2006.01)

(52) U.S. Cl.
CPC ........... C12N 15/1037 (2013.01); C12N 1/16 (2013.01); C12N 15/1089 (2013.01)

(58) Field of Classification Search
None
See application file for complete search history.

(56) References Cited

U.S. PATENT DOCUMENTS

| | | |
|---|---|---|
| 5,695,941 A | 12/1997 | Brent et al. |
| 6,057,101 A | 5/2000 | Nandabalan et al. |
| 6,083,693 A | 7/2000 | Nandabalan et al. |
| 6,187,535 B1 | 2/2001 | Legrain et al. |
| 6,395,478 B1 | 5/2002 | Nandabalan et al. |
| 6,410,239 B1 | 6/2002 | Nandabalan et al. |
| 6,423,538 B1 | 7/2002 | Wittrup et al. |
| 6,531,284 B1 | 3/2003 | Legrain et al. |
| 6,828,112 B2 | 12/2004 | Manfredi et al. |
| 6,841,352 B2 | 1/2005 | Ostanin |
| 6,913,886 B2 | 7/2005 | Legrain et al. |
| 9,005,927 B2 | 4/2015 | Hufton et al. |
| 9,034,601 B2 | 5/2015 | Hufton et al. |
| 9,139,637 B2 | 9/2015 | Wittrup et al. |
| 9,249,410 B2 | 2/2016 | Hill et al. |
| 10,017,758 B1 | 7/2018 | Peikon et al. |
| 10,385,332 B2 | 8/2019 | Hill et al. |
| 10,876,107 B2 | 12/2020 | Vigneault et al. |
| 10,988,759 B2 | 4/2021 | Baker et al. |
| 11,002,731 B2 | 5/2021 | Pfeiffer et al. |
| 11,136,573 B2 | 10/2021 | Baker et al. |
| 2003/0064477 A1 | 4/2003 | Band et al. |
| 2003/0119002 A1 | 6/2003 | Nandabalan et al. |
| 2005/0196743 A1 | 9/2005 | Ostanin et al. |
| 2005/0251871 A1 | 11/2005 | Chiaur et al. |
| 2008/0176756 A1 | 7/2008 | Siegel et al. |
| 2009/0208973 A1 | 8/2009 | Pagano |
| 2010/0075326 A1 | 3/2010 | Jin et al. |
| 2011/0071046 A1 | 3/2011 | Holt et al. |
| 2013/0008507 A1 | 1/2013 | Ko |
| 2013/0085072 A1 | 4/2013 | Bradbury et al. |
| 2017/0205421 A1 | 7/2017 | Baker et al. |
| 2021/0054365 A1 | 2/2021 | Baker et al. |
| 2021/0147831 A1 | 5/2021 | Zhang et al. |
| 2022/0025356 A1 | 1/2022 | Baker et al. |

FOREIGN PATENT DOCUMENTS

| | | |
|---|---|---|
| CA | 2666336 | 5/2008 |
| EP | 1292710 B1 | 8/2007 |
| EP | 1677113 A1 | 7/2008 |
| EP | 2436766 A1 | 4/2012 |
| WO | 2002/086120 | 3/2002 |
| WO | 2007/145661 | 12/2007 |
| WO | 2011/092233 | 8/2011 |
| WO | 2021/231013 | 11/2021 |
| WO | 2021/247572 | 12/2021 |

OTHER PUBLICATIONS

Younger et al. (PNAS 114:12116-71 supporting information) (Year: 2017).*
Tanaka et al., "Recent developments in yeast cell surface display toward extended applications in biotechnology," Applied Microbiology & Biotechnology, vol. 95, No. 3, pp. 577-591 (2012).
Terrance et al., "Sexual agglutination in Saccharomyces cerevisiae," Journal of Bacteriology, vol. 148, No. 3, pp. 889-896 (1981).
Thompson et al., "SYNZIP protein interaction toolbox: in vitro and in vivo specifications of heterospecific coiled-coil interaction domains," ACS Synthetic Biology, vol. 1, No. 4, pp. 118-129 (2012).
Vidal, "Interactome modeling," FEBS Letters, vol. 579, No. 8, pp. 1834-1838 (2005).
Wahlbom et al., "Molecular analysis of a Saccharomyces cerevisiae mutant with improved ability to utilize xylose shows enhanced expression of proteins involved in transport, initial xylose metabolism, and the pentose phosphate pathway," Applied and Environmental Microbiology, vol. 69, No. 2, pp. 740-746 (2003).
Wang et al., "A modular cell-based biosensor using engineered genetic logic circuits to detect and integrate multiple environmental signals," Biosensors and Bioelectronics, vol. 40, No. 1, pp. 368-376 (2013).
Wang et al., "Three-dimensional reconstruction of protein networks provides insight into human genetic disease," Nature Biotechnology, vol. 30, No. 2, pp. 159-164 (2012).
Weaver-Feldhaus et al., "Yeast mating for combinatorial Fab library generation and surface display," FEBS Letters, vol. 564, pp. 24-34 (2004).
Weber et al., "Emerging biomedical applications of synthetic biology," Nature Reviews Genetics, vol. 13, No. 1, pp. 21-35 (2012).
Nen et al., "Yeast surface display of trifunctional minicellulosomes for simultaneous saccharification and fermentation of cellulose to ethanol," Applied and Environmental Microbiology, vol. 76, No. 4, pp. 1251-1260 (2010).

(Continued)

Primary Examiner — Christopher M Gross
(74) Attorney, Agent, or Firm — Gardella Grace P.A.

(57) ABSTRACT

Provided herein are methods for identifying pairs of protein binding partners, mutations of which may inform the discovery of pharmaceutically useful small molecules. The methods disclosed herein may allow for the adaptation of the native protein degradation system to modulate specific disease targets at the protein level, in particular, for targets that have long been considered undruggable.

20 Claims, 20 Drawing Sheets

(56) References Cited

OTHER PUBLICATIONS

Wilson et al., "The LoxP/CRE system and genome modification," Gene Knockout Protocols, Humana Press, pp. 83-94 (2001).
Yu et al., "High-quality binary protein interaction map of the yeast interactome network." Science, vol. 322, No. 5898, pp. 104-110 (2008).
Haber, "Bisexual Mating Behavior in a Diploid of *Saccharomyces cerevisiae*: Evidence for Genetically Controlled Non-Random Chromosome Loss During Vegetative Growth," Genetics, vol. 78, pp. 843-858 (1974).
Goossens et al., "Molecular Mechanism of Flocculation Self-Recognition in Yeast and Its Role in Mating and Survival," mBio vol. 6, No. 2, e00427-15, pp. 1-16 (2015).
Suzuki, "Roles of sexual cell agglutination in yeast mass mating," Genes Genet. Syst., vol. 78, pp. 211-219 (2003).
Diener et al., "Yeast mating and image-bsed quantification of spatial pattern formation," PLOS Computational Biology, 10: e1003690, 14 pages (2014).
International Search Report and Written Opinion issued in International Application No. PCT/US2021/027111 dated Jul. 12, 2021.
International Search Report and Written Opinion issued in International Application No. PCT/US2021/035246 dated Nov. 3, 2021.
Hughes, et al., "Molecular recognition of ternary complexes: a new dimension in the structure-guided design of chemical degraders", Essays in Biochemistry, vol. 61, No. 5, pp. 505-516 (2017).
Lõoke et al., "Extraction of genomic DNA from yeasts for PCR-based applications," Biotechniques 50: 325-328 (2011).
Banta, "Replacing Antibodies: Engineering New Binding Proteins" Annual Review of Biomedical Engineering, vol. 15, pp. 93-113 (2013).
Barton et al., "Why sex and recombination?" Science 281.5385, pp. 1986-1990 (1998).
Bender et al., "Pheromones and pheromone receptors are the primary determinants of mating specificity in the yeast *Saccharomyces cerevisiae*," Genetics, vol. 121, pp. 463-476 (1989).
Boder et al., "Yeast surface display of a noncovalent MHC class II heterodimer complexed with antigenic peptide," Biotechnology and Bioengineering, vol. 92, No. 4, pp. 485-491 (2005). https://doi.org/10.1002/bit 20616.
Boder et al., "Yeast surface display system for antibody engineering," Immunotechnology, vol. 2.4, p. 283 (1996).
Cappellaro et al., "Mating type-specific cell-cell recognition of *Saccharomyces cerevisiae*: cell wall attachment and active sites of a- and alpha-agglutinin," EMBO Journal, vol. 13, No. 20, pp. 4737-4744 (1994).
Cardinale et al., "Contextualizing context for synthetic biology-identifying causes of failure of synthetic biological systems," Biotechnology Journal, vol. 7, p. 7, pp. 856-866 (2012).
Casini et al., "R2oDNA designer: computational design of biologically neutral synthetic DNA Sequences." ACS Synthetic Biology, vol. 3, No. 8, pp. 525-528 (2014).
Dhan et al., "Isolation and genetic analysis of Saccharomyces cerevisiae mutants supersensitive to G1 arrest by a factor and alpha factor pheromones," Molecular and Cellular Biology, vol. 2, No. 1, pp. 11-20 (1982).
Chao et al., "Fine epitope mapping of anti-epidermal growth factor receptor antibodies through random mutagenesis and yeast surface display," Journal of molecular biology, vol. 342, No. 2, pp. 539-550 (2004).
Chee et al., "New and redesigned pRS plasmid shuttle vectors for genetic manipulation of *Saccharomyces cerevisiae*," G3: Genes | Genomes | Genetics, vol. 2, No. 5, pp. 515-526 (2012).
Chen, et al., "Cell-cell fusion," FEBS letters, vol. 581, No. 11, pp. 2181-2193 (2007).
Chenevert et al., "Identification of genes required for normal pheromone-induced cell polarization in *Saccharomyces cerevisiae*," Genetics, vol. 136, No. 4, pp. 1287-1296 (1994).

Cherf et al., "Applications of yeast surface display for protein engineering", Methods in Molecular Biology, vol. 1319, pp. 155-175 (2015).
Colegrave, "Sex releases the speed limit on evolution," Nature, vol. 420, No. 6916, pp. 664-666 (2002).
Daar et al., "Top ten biotechnologies for improving health in developing countries," Nature Genetics, vol. 32, No. 2, pp. 229-232 (2002).
Daniel et al., "Synthetic analog computation in living cells," Nature, vol. 497, pp. 619-623 (2013).
Daugherty et al., "Antibody affinity maturation using bacterial surface display," Protein Engineering, vol. 11, No. 9, pp. 825-832 (1998).
Dunham, "Synthetic ecology: a model system for cooperation," Proceedings of the National Academy of Sciences, vol. 104, No. 6, pp. 1741-1742 (2007).
Dunn et al., "Natural and sexual selection act on different axes of variation in avian plumage color," Science Advances, vol. 1.2, e1400155, 7 pages (2015).
Eby et al., "Characterization, performance, and applications of a yeast surface display-based biocatalyst", RSC Advances, vol. 5, p. 19166-19175 (2015).
Fletcher et al., "A basis set of de novo coiled-coil peptide oligomers for rational protein design and synthetic biology," ACS Synthetic Biology, vol. 1, pp. 240-250 (2012).
Gera et al., "Protein selection using yeast surface display," Methods. vol. 60, No. 1, pp. 15-26 (2013).
Greig et al., "Hybrid speciation in experimental populations of yeast," Science, vol. 298, pp. 1773-1775 (2002).
Guo et al., "A *Saccharomyces* gene family involved in invasive growth, cell-cell adhesion, and mating," Proceedings of the National Academy of Sciences, vol. 97, No. 22, p. 12158-12163 (2000).
Haber, "Mating-type genes and MAT switching in *Saccharomyces cerevisiae*," Genetics, vol. 191, pp. 33-64 (2012).
Head et al., "Female mate preferences for male body size and shape promote sexual isolation in threespine sticklebacks," Ecology and Evolution, vol. 3, pp. 2183-2196 (2013).
Howitt et al., "Technologies for global health," The Lancet, vol. 380, pp. 507-535 (2012).
Huang et al., "Conserved WCPL and CX4C domains mediate several mating adhesin interactions in *Saccharomyces cerevisiae*," Genetics, vol. 182, pp. 173-189 (2009).
Ito et al., "Transformation of intact yeast cells treated with alkali cations,"Journal of Bacteriology, vol. 153, No. 1, pp. 163-168 (1983).
Jackson et al., "Courtship in *Saccharomyces cerevisiae*: an early cell-cell interaction during mating," Molecular and Cellular Biology, vol. 10, No. 5, pp. 2202-2213 (1990).
James et al., "Biophysical mechanism of T-cell receptor triggering in a reconstituted system," Nature, vol. 487, pp. 64-69 (2012).
Kaster et al., "Hygromycin B resistance as dominant selectable marker in yeast," Current Genetics, vol. 8, pp. 1984, pp. 353-358 (1984).
Keddar et al., "Color ornaments and territory position in king penguins," Behavioural Processes, vol. 119, pp. 32-37, (2015).
Khakhar et al., "Cell-Cell Communication in Yeast Using Auxin Biosynthesis and Auxin Responsive CRISPR Transcription Factors," ACS Synthetic Biology (2015).
Malleshaiah et al., "The scaffold protein Ste5 directly controls a switch-like mating decision in yeast," Nature, vol. 465, pp. 101-105 (2010).
Martins et al., "Evolution and stability of ring species," Proceedings of the National Academy of Sciences, vol. 110, No. 13, pp. 5080-5084 (2013).
Miura et al., "Enzyme evolution by yeast cell surface engineering", Methods in Molecular Biology, vol. 1319, pp. 217-232(2015).
Nasmyth, "Molecular genetics of yeast mating type," Annual Review of Genetics, vol. 16, pp. 439-500 (1982).
Parrish et al., "Yeast two-hybrid contributions to interactome mapping," Current Opinion in Biotechnology, vol. 17, pp. 387-393 (2006).

(56) References Cited

OTHER PUBLICATIONS

Put et al., "The heat resistance of ascospores of four *Saccharomyces* spp. isolated from spoiled heat-processed soft drinks and fruit products," Journal of Applied Bacteriology, vol. 52, No. 2, pp. 235-243 (1982).

Richman et al., "Biosensor detection systems: engineering stable, high-affinity bioreceptors by yeast surface display," Methods in Molecular Biology, vol. 504, pp. 323-350 (2009).

Rodriguez et al., "Diversification under sexual selection: the relative roles of mate preference strength and the degree of divergence in mate preferences," Ecology Letters, vol. 16, No. 8, pp. 964-974 (2013).

Safran et al., "Contributions of natural and sexual selection to the evolution of premating reproductive isolation: a research agenda," Trends in Ecology & Evolution, vol. 28, No. 11, pp. 643-650 (2013).

Sauer, "Functional expression of the cre-lox site-specific recombination system in the yeast *Saccharomyces cerevisiae*," Molecular and Cellular Biology, vol. 7, No. 6, pp. 2087-2096 (1987).

Segall, "Polarization of yeast cells in spatial gradients of alpha mating factor," Proceedings of the National Academy of Sciences, vol. 90, No. 18, pp. 8332-8336 (1993).

Shou et al., "Synthetic cooperation in engineered yeast populations," Proceedings of the National Academy of Sciences, vol. 104, No. 6, pp. 1877-1882 (2007).

Sreekrishna et al., "Construction of strains of *Saccharomyces cerevisiae* that grow on lactose," Proceedings of the National Academy of Sciences, vol. 82, No. 23, pp. 7909-7913 (1985).

Sundstrom, "Adhesins in Candida albicans," Current Opinion in Microbiology, vol. 2, No. 4, pp. 353-357 (1999).

Rothstein R., "Targeting, disruption, replacement, and allele rescue: integrative DNA transformation in yeast," Methods Enzymol. 1991;194:281-301. doi: 10.1016/0076-6879(91)94022-5. PMID: 2005793.

Dura et al., "Spatially and temporally controlled immune cell interactions using microscale tools," Current Opinion in Immunology 35 (2015): 23-29.

Lipke, et al., "Sexual Agglutination in Budding Yeasts: Structure, Function, and Regulation of Adhesion Glycoproteins," Microbiological Reviews (1992): 180-194.

Pettersen et al., "UCSF ChimeraX: Structure visualization for researchers, educators, and developers," Protein Science 30.1 (2021): 70-82.

Maute et al., "Engineering high-affinity PD-1 variants for optimized immunotherapy and immuno-PET imaging," Proceedings of the National Academy of Sciences 112.47 (2015): E6506-E6514.

Altschul et al., "Basic local alignment search tool," Journal of Molecular Biology 215.3: 403-410 (1990).

Amarasinghe et al., "Opportunities and challenges in long-read sequencing data analysis," Genome Biology 21:1-16 (2020).

Younger et al., "High-throughput characterization of protein-protein interactions by reprogramming yeast mating," Proceedings of the National Academy of Sciences 114:12166-12171 (2017).

Fields et al., "A novel genetic system to detect protein-protein interactions," Nature 340, 245-246 (1989). https://doi.org/10.1038/340245a0.

Yu et al., "Next-generation sequencing to generate interactome datasets," Nature Methods 8(6): 478-480 (2011).

Hastie et al., "Yeast two-hybrid interaction partner screening through in vivo Cre-mediated Binary Interaction Tag generation," Nucleic Acids Research 35(21): e141 (2007).

Yachie et al., "Pooled-matrix protein interaction screens using Barcode Fusion Genetics," Molecular Systems Biology 12:863 (2016).

Chen et al., "Exhaustive benchmarking of the yeast two-hybrid system," Nat Methods 7, 667-668 (2010). https://doi.org/10.1038/nmeth0910-667.

Braun et al., "An experimentally derived confidence score for binary protein-protein interactions." Nature Methods 6(1):91-97.

Smith, "Filamentous Fusion Phage: Novel Expression Vectors That Display Cloned Antigens on the Virion Surface," Science 228:1315-1317 (1985). https://doi.org/10.1126/science.4001944.

Boder et al., "Yeast surface display for screening combinatorial polypeptide libraries," Nature Biotechnology 15:553-557 (1997).

Perfetto et al., "Seventeen-colour flow cytometry: unravelling the immune system," Nat. Rev. Immunol. 4:648-655 (2004).

Gu et al., "Multiplex single-molecule interaction profiling of DNA-barcoded proteins," Nature 515:554-557 (2014). https://doi.org/10.1038/nature13761.

Roy et al., "The AGA1 product is involved in cell surface attachment of the *Saccharomyces cerevisiae* cell adhesion glycoprotein a-agglutinin," Molecular and Cellular Biology 11(8): 4196-4206 (1991).

Dranginis et al., "A Biochemical Guide to Yeast Adhesins: Glycoproteins for Social and Antisocial Occasions," Microbiology and Molecular Biology Reviews, 71(2): 282-294 (2007).

Zhao et al., "Interaction of a-Agglutinin and a-Agglutinin, *Saccharomyces cerevisiae* Sexual Cell Adhesion Molecules," Journal of Bacteriology, 183(9):2874-2880 (2001).

Herskowitz, "Life cycle of the budding yeast *Saccharomyces cerevisiae*," Microbiological Reviews 52(4): 536-553 (1988).

Boder et al., "Directed evolution of antibody fragments with monovalent femtomolar antigen-binding affinity," Proceedings of the National Academy of Sciences 97(20): 10701-10705 (2000).

Huang et al., "Secretion and Surface Display of Green Fluorescent Protein Using the Yeast *Saccharomyces cerevisiae*," Biotechnol Progress, 21: 349-357 (2005). https://doi.org/10.1021/bp0497482.

Kim et al., "Directed evolution of the epidermal growth factor receptor extracellular domain for expression in yeast," Proteins 62(4): 1026-1035 (2006).

Adams et al., "The Bcl-2 Protein Family: Arbiters of Cell Survival," Science 281:1322-1326 (1998). https://doi.org/10.1126/science.281.5381.1322.

Chen et al., "Differential Targeting of Prosurvival Bcl-2 Proteins by Their BH3-Only Ligands Allows Complementary Apoptotic Function," Molecular Cell 17: 393-403 (2005).

Procko et al., "A Computationally Designed Inhibitor of an Epstein-Barr Viral Bcl-2 Protein Induces Apoptosis in Infected Cells." Cell, 157:1644-1656 (2014).

Berger et al. "Computationally designed high specificity inhibitors delineate the roles of BCL2 family proteins in cancer," eLife 5:e20352 (2016).

McIsaac et al., "Synthetic gene expression perturbation systems with rapid, tunable, single-gene specificity in yeast," Nucleic Acids Research 41(4): e57 (2013).

Day et al., "Solution structure of prosurvival Mcl-1 and characterization of its binding by proapoptotic BH3-only igands," Journal of Biological Chemistry 280:4738-4744 (2005).

Sauer et al., "Site-specific DNA recombination in mammalian cells by the Cre recombinase of bacteriophage P1," Proceedings of the National Academy of Sciences 85: 5166-5170 (1988).

Louvion et al., "Fusion of GAL4-VP16 to a steroid-binding domain provides a tool for gratuitous induction of galactose-responsive genes in yeast," Gene, vol. 131, Issue 1, pp. 129-134 (1993). https://doi.org/10.1016/0378-1119(93) 90681-R.

Gibson et al. "Enzymatic assembly of DNA molecules up to several hundred kilobases," Nature Methods 6: 343-345 (2009).

Sanger et al., "DNA sequencing with chain-terminating inhibitors," Proceedings of the National Academy of Sciences 74: 5463-5467 (1977).

Araki et al., "Site-directed integration of the ere gene mediated by Cre recombinase using a combination of mutant lox sites," Nucleic Acids Research 30: e103 (2002).

Bentley et al., "Accurate whole human genome sequencing using reversible terminator chemistry," Nature 456: 53-59 (2008).

van Delft et al., "How the Bcl-2 family of proteins interact to regulate apoptosis," Cell Research 16:203-213 (2006).

Lee et al., "A highly characterized yeast toolkit for modular, multipart assembly," ACS Synthetic Biology 4: 975-986 (2015).

Wingler et al., "Reiterative recombination for the in vivo assembly of libraries of multigene pathways," Proceedings of the National Academy of Sciences 108: 15135-15140 (2011).

(56) References Cited

OTHER PUBLICATIONS

Gai et al., "Yeast surface display for protein engineering and characterization," Current Opinion in Structural Biology 17:467-473 (2007).
Wadle et al., "Serological identification of breast cancer-related antigens from a *Saccharomyces cerevisiae* surface display library," International Journal of Cancer 117: 104-113 (2005).
van den Beucken et al., "Affinity maturation of Fab antibody fragments by fluorescent-activated cell sorting of yeast-displayed libraries," FEBS Letters 546: 288-294 (2003).
Strauch et al., "Computational design of a pH-sensitive IgG binding protein," Proceedings of the National Academy of Sciences 111: 675-680 (2014).
Lee et al., "Bioengineered protein-based nanocage fordrug delivery," Advanced Drug Delivery Reviews 106: 157-171 (2016). https://doi.org/10.1016/j.addr.2016.03.002.
Wells et al., "Reaching for high-hanging fruit in drug discovery at protein-protein interfaces," Nature 450: 1001-1009 (2007).
Xie et al., "Accelerated and adaptive evolution of yeast sexual adhesins," Molecular Biology and Evolution 28: 3127-3137 (2011).
Balagaddé et al., "A synthetic *Escherichia coli* predator-prey ecosystem," Molecular Systems Biology 4: 187, 8 pages (2008).
Gietz, et al., "High-efficiency yeast transformation using the LiAc/SS carrier DNA/PEG method," Nature Protocols 2: 31-34 (2007).
Boeke et al., "A positive selection for mutants lacking orotidine-5'-phosphate decarboxylase activity in yeast: 5-fluoro-orotic acid resistance," Molecular and General Genetics 197: 345-346 (1984).

\* cited by examiner

HIGH-THROUGHPUT SCREENING METHODS TO IDENTIFY SMALL MOLECULE TARGETS

RELATED APPLICATIONS

This application is a continuation of and claims priority to U.S. patent application Ser. No. 17/607,801, entitled "HIGH-THROUGHPUT SCREENING METHODS TO IDENTIFY SMALL MOLECULE TARGETS," filed Oct. 29, 2021, which is a U.S. National Stage Entry of International Application No. PCT/US2021/027111, entitled "HIGH-THROUGHPUT SCREENING METHODS TO IDENTIFY SMALL MOLECULE TARGETS," filed Apr. 13, 2021, which claims priority to U.S. Provisional Patent Application Ser. No. 63/023,181 filed May 11, 2020. All above-identified applications are hereby incorporated by reference in their entireties.

BACKGROUND

Targeting biological processes within cells for pharmacological intervention is the central goal for drug discovery. The process of identifying an inhibitory drug for a specific target protein must meet the demands of high affinity for the target, high potency and selectivity for the target effect, and identifying a dose that maintains high enough drug concentration at the intended tissue to sustain the desired pharmacological effect, while minimizing toxicity and unintended off-target effects. Small molecules are attractive candidates for modulation of intracellular targets because of their ability to cross plasma membranes, access a wide range of tissues and sites of action, effect multiple targets simultaneously, and be produced economically at scale.

The ubiquitin-proteasome system (UPS) is an endogenous intracellular protein degradation system that is highly conserved across eukaryotic species. Polyubiquitylation of a target protein by an E3 ubiquitin ligase destines the target protein for subsequent destruction by the proteasome, a multi-unit cylindrical structure that proteolytically breaks down its target protein substrates. This highly regulated system of protein degradation is critical for cellular homeostasis and may be disrupted in various disease states. Coopting this native protein degradation system to modulate specific disease targets at the protein level is an active area of current research and has great therapeutic potential, especially for targets that have long been considered "undruggable."

The transfer of ubiquitin molecules to a target protein, the substrate, by an E3 ubiquitin ligase is mediated by both substrate recognition and proximity. In the native context, several different mechanisms of substrate recognition exist, most of which involve degrons—short amino acid sequences or chemical motifs on the target protein that are recognized by the E3 ubiquitin ligase and mediate interaction between the ligase and the target protein substrate. N-degrons at the N-terminus of target proteins may be revealed by proteolytic cleavage and mediate recognition by E3 ubiquitin ligase. Phosphodegrons are converted into their active and recognized form by phosphorylation of a tyrosine, serine, or threonine residue of the target protein. A ubiquitin ligase may only recognize the phosphorylated version of the substrate due to stabilization within the ligase-substrate binding site—unphosphorylated substrates are not recognized. Further, oxygen, small molecules, or structural motifs of the substrate may also influence degron recognition.

Previous work demonstrated that a small molecule known to interact with a target protein could be linked to an epitope known to interact with an E3 ubiquitin ligase, mediating proximity-based interaction between the target protein and E3 ubiquitin ligase, and thereby triggering cellular degradation of the target protein. So-called "proteolysis-targeting chimera," or PROTACs, demonstrated that artificial stabilization of the ternary complex between the E3 ubiquitin ligase and the degradation target resulted in successful degradation of the target. PROTACs consist of two small molecules connected by a linker. However, the relatively high molecular weight, physiochemical properties, and pharmaceutical properties of most PROTACs make them unsuitable as candidates for small molecule drugs.

Recently, a class of small molecules has been shown to mediate or induce interaction between an E3 ubiquitin ligase and its target protein substrate. Thalidomide analogs, including lenalidomide and pomalidomide, bind to the E3 ubiquitin ligase $CRL4^{CRBN}$, and induce degradation of various targets including Ikaros (IKZF1), Aiolos, and CK1α, with surprising versatility and selectivity. These discoveries, among others, illuminated opportunities to identify small molecules that may agonize protein-protein interactions, e.g., between an E3 ubiquitin ligase and a novel target protein, and identify therapeutic targets. For example, a small molecule may be identified or designed to chemically induce UPS-mediated degradation of undruggable proteins that are immune to traditional small molecule inhibitors.

The methods disclosed herein include several distinct advantages over existing protein-protein interaction screening approaches, e.g., phage display or yeast surface display. First, the methods disclosed herein allow for library-by-library screening, i.e., interrogating interactions between one plurality of potential protein binding partners and another plurality of protein binding partners en masse in a high-throughput way. Phage and yeast surface display techniques can only screen binding against a limited number of targets simultaneously due to the spectral resolution of existing fluorescent reporters. For example, such techniques would be limited to screening for targets of only a few E3 ubiquitin ligases at a time. The methods disclosed herein enable screening for targets of many variants of many E3 ubiquitin ligases at a time in a single assay.

Second, the methods disclosed herein provide quantitative results of interaction intensities at a very fine level of resolution. Existing approaches may be limited to only detecting strong interactions that exceed a certain threshold established by the investigator and may enrich for only those strong interactions. The methods disclosed herein may detect subtle modulations in binding affinity between variants of potential protein binding partners, for example, during a screen of a site-saturation mutagenesis (SSM) library of one protein binding partner against a site-saturation mutagenesis (SSM) library of a second protein binding partner. Modest and quantitative effects of mutations at the binding interface may be detected by the methods disclosed herein that would have been otherwise undetected by other screening platforms. In addition, the methods disclosed herein are particularly well-suited to detecting and identifying potentially novel substrates for targeting proteins, for example, novel substrates for E3 ubiquitin ligases. The interaction between an E3 ubiquitin ligase and a previously unknown substrate represent attractive candidates for small molecule discovery and design.

Finally, the methods disclosed herein are high-throughput, fast, and cost-effective. All protein binding partners in the extensive library-by-library studies enabled by the methods disclosed herein are genetically encoded and produced by yeast cells. No expensive and laborious expression and purification of recombinant proteins is required. Thousands of potential interactions are screened quickly and affordably in a single assay.

For the reasons discussed above, there is thus a need for rational high-throughput methods to discover pairs of protein binding partners, e.g., an E3 ubiquitin ligase and its target protein substrate, the interaction of which may be amenable to modulation by small molecules. After such a pair of protein binding partners is discovered, high-throughput small molecule screening campaign or rational drug design based on the crystal structures of the protein-protein interface. The methods disclosed herein meet that need.

SUMMARY

In some embodiments, methods are provided for assaying protein-protein interactions, the method comprising providing a plurality of polypeptide ubiquitin ligase species expressed and displayed on the surface of a first plurality of recombinant haploid yeast cells, wherein the first plurality of polypeptides ubiquitin ligase species comprises a library of wild-type polypeptide ubiquitin ligase species and mutant polypeptide ubiquitin ligase species that have been modified at one or more amino acid residue positions by mutagenesis; providing a plurality of polypeptide substrate species expressed and displayed on the surface of a second plurality of recombinant haploid yeast cells, wherein the plurality of polypeptide substrate species comprises a library of wild-type polypeptide substrate species and mutant polypeptide substrates species that have been modified at one or more amino acid residue positions by mutagenesis; combining the first plurality of recombinant haploid yeast cells and the second plurality of recombinant haploid yeast cells in a liquid medium to produce a culture; growing the culture for a time and under conditions such that one or more interactions between one or more of the plurality of polypeptide ubiquitin ligase species and one or more of the plurality of polypeptide substrate species mediates one or more mating events between one or more of the first plurality of recombinant haploid yeast cells and one or more of the second plurality of recombinant haploid yeast cells to produce one or more diploid yeast cells; determining, based on the number of mating events in the culture, the strength of the interactions between one or more of the plurality of polypeptide ubiquitin ligase species and one or more of the plurality of polypeptide substrate species; and identifying pairs of polypeptides wherein one or both of one of the polypeptide ubiquitin ligase species and one of the polypeptide substrate species have been modified at one or more amino acid residue positions by mutagenesis and the strength of the interaction ($K_D$) between the polypeptide ubiquitin ligase species and the polypeptide substrate species is stronger or weaker than the interaction between the corresponding wild-type polypeptide species by at least 10%.

In further embodiments, the strength of the interaction ($K_D$) between the polypeptide ubiquitin ligase species and the polypeptide substrate species is stronger or weaker than the interaction between the corresponding wild-type polypeptide species by at least 25%. In yet further embodiments, the one or more polypeptide ubiquitin ligase species are E3 ubiquitin ligase species. In some embodiments, the one or more polypeptide substrate species comprise a known or predicted degron motif. In other embodiments one or more of the first plurality of polypeptides have been modified at one or more amino acid residue positions by mutagenesis to introduce steric bulk to a domain of the polypeptide.

In other embodiments, the method further comprises computationally modeling the interface between the polypeptide ubiquitin ligase species and the polypeptide substrate species that have been modified at one or more amino acid residue positions by mutagenesis in order to determine the structure of the interface between the polypeptide ubiquitin ligase species and the polypeptide substrate species. In further embodiments the growing step further comprises growing the culture in the presence of one or more small molecules, proteins, peptides, pharmaceutical compound, or other chemical entities.

In yet other embodiments, the identifying step further comprises identifying pairs of polypeptides wherein the strength of the interaction ($K_D$) between the polypeptide ubiquitin ligase species and the polypeptide substrate species is stronger or weaker in the presence of one or more small molecules, proteins, peptides, pharmaceutical compound, or other chemical entities than the interaction between the polypeptide ubiquitin ligase species and the polypeptide substrate species in the absence of the one or more small molecules, proteins, peptides, pharmaceutical compound, or other chemical entities by at least 10%.

In some embodiments the plurality of polypeptides ubiquitin ligase species are wild-type ubiquitin ligase species and the plurality of polypeptide substrate species are wild type polypeptide substrate species. In other embodiments an interaction between one of the plurality of polypeptides ubiquitin ligase species and one of the plurality of polypeptide substrate species is detected in the presence of one or more small molecules, proteins, peptides, pharmaceutical compound while no interaction is detected between one of the plurality of polypeptides ubiquitin ligase species and one of the plurality of polypeptide substrate species in the absence of the small molecule, protein, peptide, pharmaceutical compound, or other chemical entity.

In other embodiments, methods are provided for assaying protein-protein interactions, the method comprising providing a plurality of first protein binding partners expressed and displayed on the surface of a first plurality of recombinant haploid yeast cells, wherein the plurality of first protein binding partners comprises a library of wild-type polypeptide species and mutant polypeptide species that have been modified at one or more amino acid residue positions by mutagenesis; providing a plurality of second protein binding partners expressed and displayed on the surface of a second plurality of recombinant haploid yeast cells, wherein the plurality of second protein binding partners comprises a library of wild-type polypeptide species and mutant polypeptide species that have been modified at one or more amino acid residue positions by mutagenesis; combining the first plurality of recombinant haploid yeast cells and the second plurality of recombinant haploid yeast cells in a liquid medium to produce a culture; growing the culture for a time and under conditions such that one or more interactions between one or more of the plurality of first protein binding partners and one or more of the plurality of second protein binding partners mediates one or more mating events between one or more of the first plurality of recombinant haploid yeast cells and one or more of the second plurality of recombinant haploid yeast cells to produce one or more diploid yeast cells; determining, based on the number of mating events in the culture, the strength of the interactions between one or more of the plurality of first protein binding partners and one or more of the plurality of second protein binding partners; and identifying pairs of polypeptides wherein one or both of one of the first protein binding partners and one of the second protein binding partners have been modified at one or more amino acid residue positions by mutagenesis and the strength of the interaction ($K_D$) between the first protein binding partner and the second protein binding partner is stronger or weaker than the interaction between the corresponding wild-type polypeptide species by at least 10%.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings.

DETAILED DESCRIPTION OF ILLUSTRATIVE EMBODIMENTS

Figure 1:
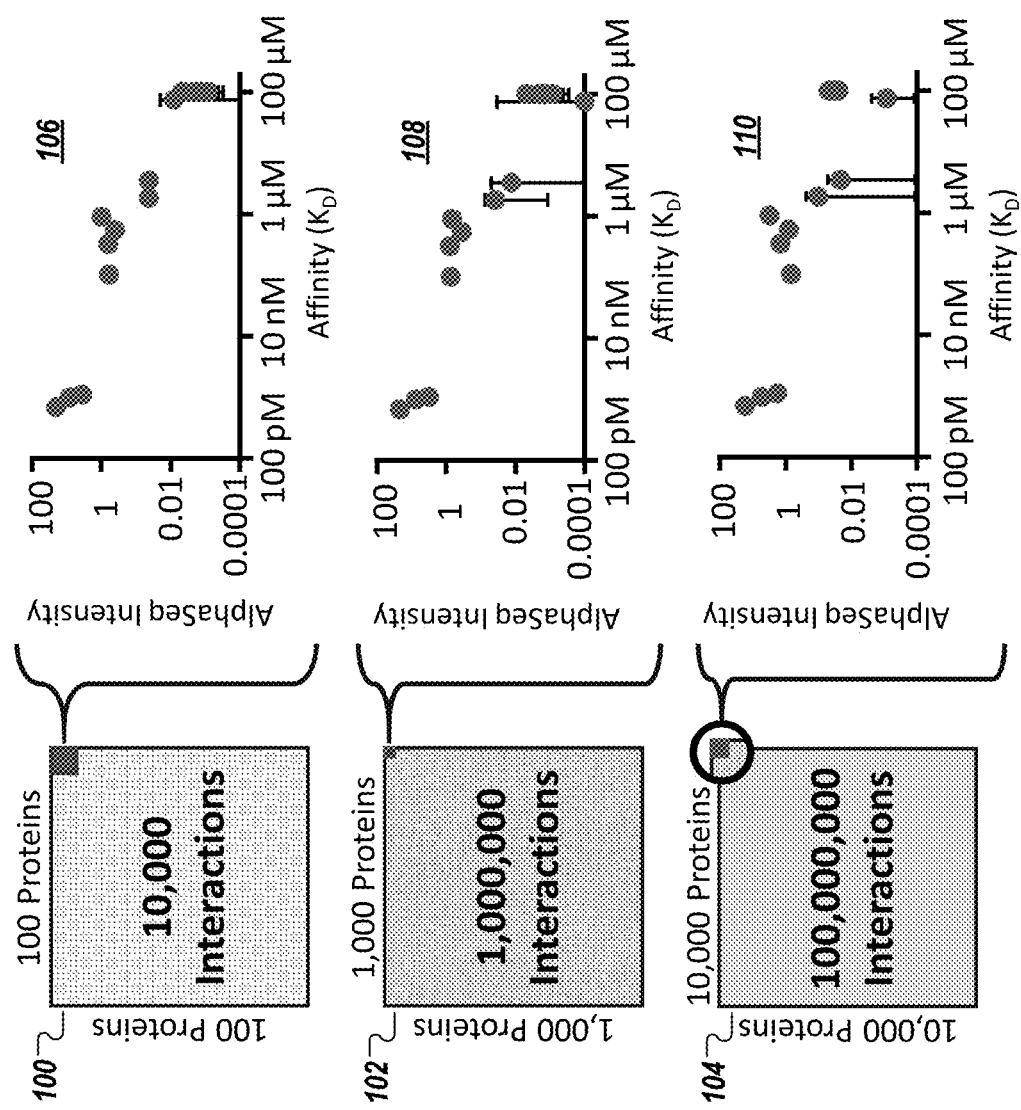
FIG. 1 depicts a series of charts showing the library-by-library screening capacity and resolution of the methods disclosed herein.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, cell culture, biochemistry, and sequencing technology, which are within the skill of those who practice in the art. Such conventional techniques include bacterial, fungal, and mammalian cell culture techniques and screening assays. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual;* Dieffenbach, Dveksler, Eds. (2003), *PCR Primer: A Laboratory Manual;* Bowtell and Sambrook (2003), *DNA Microarrays: A Molecular Cloning Manual;* Mount (2004), *Bioinformatics: Sequence and Genome Analysis;* Sambrook and Russell (2006), *Condensed Protocols from Molecular Cloning: A Laboratory Manual;* and Sambrook and Russell (2002), *Molecular Cloning: A Laboratory Manual* (all from Cold Spring Harbor Laboratory Press); Stryer, L. (1995) *Biochemistry* (4th Ed.) W. H. Freeman, New York N.Y.; Gait, *"Oligonucleotide Synthesis: A Practical Approach"* 1984, IRL Press, London; Nelson and Cox (2000), *Lehninger, Principles of Biochemistry* $3^{rd}$ Ed., W. H. Freeman Pub., New York, N.Y.; Berg et al. (2002) *Biochemistry*, $5^{th}$ Ed., W. H. Freeman Pub., New York, N.Y.; all of which are herein incorporated in their entirety by reference for all purposes.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TTAGCTGG-3'.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements, e.g., barcode sequences, gene expression cassettes, coding sequences, promoters, enhancers, transcription factor binding sites, where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, puromycin, hygromycin, blasticidin, and G418 may be employed. A selectable marker may also be an auxotrophy selectable marker, wherein the cell strain to be selected for carries a mutation that renders it unable to synthesize an essential nutrient. Such a strain will only grow if the lacking essential nutrient is supplied in the growth medium. Essential amino acid auxotrophic selection of, for example, yeast mutant strains, is common and well-known in the art. "Selective medium" as used herein refers to cell growth medium to which has been added a chemical compound or biological moiety that selects for or against selectable markers or a medium that is lacking essential nutrients and selects against auxotrophic strains.

As used herein, the term "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, BACs, YACs, PACs, synthetic chromosomes, among others.

As used herein, "affinity" is the strength of the binding interaction between a single biomolecule to its ligand or binding partner Affinity is usually measured and described using the equilibrium dissociation constant, $K_D$. The lower the $K_D$ value, the greater the affinity between the protein and its binding partner Affinity may be affected by hydrogen bonding, electrostatic interactions, hydrophobic and Van der Waals forces between the binding partners, or by the presence of other molecules, e.g., binding agonists or antagonists.

As used herein, "site saturation mutagenesis" (SSM), refers to a random mutagenesis technique used in protein engineering and molecular biology, wherein a codon or set of codons is substituted with all possible amino acids at the position in the polypeptide. SSM may be performed for one codon, several codons, or for every position in the protein. The result is a library of mutant proteins representing the full complement of possible amino acids at one, several, or every amino acid position in a polypeptide. In some implementations, one or more sites in a polypeptide sequence may be changed to a 1, 2, 3, 4, 5, 6, 7, 8, 9, 10, 11, 12, 13, 14, 15, 16, 17, 18, or 19 different amino acid residues to produce a library of variant polypeptide sequences.

As used herein, "targeting protein" refers to a first protein binding partner which acts on a second protein binding partner. "Target protein" refers to a second protein binding partner that is acted upon by a first protein binding partner. In some implementations a targeting protein may be an E3 ubiquitin ligase and a target protein may be a canonical substrate of the E3 ubiquitin ligase. In other implementations, a target protein may be a novel, previously uncharacterized, or putative substrate of the E3 ubiquitin ligase. In other implementations, a target protein may be a peptide containing a known or predicted degron motif. As used herein, "targeting protein" and "target protein" may each comprise full-length proteins, truncated proteins, high-throughput oligonucleotide-encoded polypeptides, truncated polypeptide motifs, or known or predicted degron motifs. As used herein, "targeting protein" and "target protein" may comprise polypeptides that are 1-50, 50-100, 100-500, 500-1000, or more than 1000 amino acid residues in length.

In some implementations, the method comprises a first protein binding partner and a library of second protein binding partners. The first protein binding partner may be a targeting protein. In other implementations, the first protein binding partner may be, for example, an E3 ubiquitin ligase. The library of second protein binding partners may comprise, for example, polypeptide substrate species. The second library of protein binding partners may further comprise, for example, previously known full-length mapped E3 ubiquitin ligase substrate domains; high-throughput oligo-encodable truncated E3 ubiquitin ligase substrates; E3 ubiquitin ligase substrate species that have been modified by site saturation mutagenesis; previously defined degron motifs; or computationally-predicted degron motifs. The library of second protein binding partners may comprise a plurality of user-designated mutants of a target protein and the wild-type target protein. The plurality of user-designated mutants of a target protein may comprise variants of the target protein with 1, 2, 3, 4, 5, 6, 7, 8, 9, 10, or more amino acid substitutions. The amino acid substitutions may be chosen to introduce steric bulk to the target protein and wild-type amino acids may be substituted with natural or non-natural amino acids. The amino acid substitutions may be generated by site saturation mutagenesis. The first protein binding partner and the library of second protein binding partners are assayed for binding affinity, such that affinity is measured for interaction between the first protein binding partner and each of the plurality of user-designated mutants individually, in a parallelized high-throughput manner. Members of the library of second protein binding partners that are found to have a binding affinity with the first protein binding partner that is higher than the binding affinity of the wild-type target protein and the first protein binding partner are identified and selected for further study.

In some implementations wherein a first protein binding partner and a library of second protein binding partners are assayed for binding affinity, the assay may be phage display, yeast surface display, or another parallelized high-throughput method.

In other implementations, the method comprises a library of first protein binding partners and a library of second protein binding partners. The library of first protein binding partners may comprise, for example, polypeptide E3 ubiquitin ligase species. The first library of protein binding partners may further comprise, for example, full-length E3 ubiquitin ligases with mapped domains; high-throughput user-designed or randomly generated oligo-encodable truncated E3 ubiquitin ligase domains; or polypeptide E3 ubiquitin ligase species that have been modified by site saturation mutagenesis, The library of first protein binding partners may comprise a plurality of user-designated mutants of a targeting protein and a wild-type targeting protein. The plurality of user-designated mutants of the targeting protein may comprise variants of the targeting protein with 1, 2, 3, 4, 5, 6, 7, 8, 9, 10, or more amino acid substitutions. The amino acid substitutions may be chosen to introduce steric bulk to the targeting protein and wild-type amino acids may be substituted with natural or non-natural amino acids. The amino acid substitutions may be chosen to mimic phosphorylation or other post-translational modifications. The amino acid substitutions may be generated by targeted, random, or site saturation mutagenesis. The library of second protein binding partners may comprise, for example, polypeptide substrate species. The second library of protein binding partners may further comprise, for example, previously known full-length mapped E3 ubiquitin ligase substrate domains; high-throughput oligo-encodable truncated E3 ubiquitin ligase substrates; E3 ubiquitin ligase substrate species that have been modified by mutagenesis; previously defined degron motifs; or computationally-predicted or otherwise predicted degron motifs. The library of second protein binding partners may comprise a plurality of user-designated mutants of a target protein and the wild-type target protein. The plurality of user-designated mutants of the target protein may comprise variants of the target protein with 1, 2, 3, 4, 5, 6, 7, 8, 9, 10, or more amino acid substitutions. The amino acid substitutions may be chosen to introduce steric bulk to the target protein and wild-type amino acids may be substituted with natural or non-natural amino acids. The amino acid substitutions may be chosen to mimic phosphorylation or other post-translational modifications. The amino acid substitutions may be generated by targeted, random, or site saturation mutagenesis. The library of first protein binding partners and the library of second protein binding partners are assayed for binding affinity, such that affinity is measured for interaction between each of the plurality of mutant first protein binding partners and each of the plurality of mutant second protein binding partners pair-wise individually in a parallelized high-throughput manner. Pairs comprising a member chosen from the library of first protein binding partners and a member chosen from the library of second protein binding partners that are found to have a binding affinity that is higher than the binding affinity of the wild-type targeting protein and the wild-type target protein are identified and selected for further study.

In some implementations, pairs of protein-binding partners comprising a member chosen from the library of first protein binding partners and a member chosen from the library of second protein binding partners are identified by the methods disclosed herein to have a binding affinity that is higher than the binding affinity of the wild-type targeting protein and the wild-type target protein. The pair of protein-binding partners may comprise a mutant targeting protein and a wild-type target protein; a wild-type target protein and a mutant target protein; or a mutant targeting protein and a mutant target protein. In some implementations, the pair of protein-binding partners identified by the methods disclosed herein to have a binding affinity that is higher than the binding affinity of the wild-type targeting protein and the wild-type target protein may have a binding affinity that is higher than the binding affinity of the wild-type targeting protein and the wild-type target protein by at least 1%, 2%, 3%, 4%, 5%, 6%, 7%, 8%, 9%, 10%, 20%, 30%, 40%, 50%, 100%, 500%, 1000%, or values therebetween. In other implementations, the pair of protein-binding partners identified by the methods disclosed herein to have a binding affinity that is less than the binding affinity of the wild-type targeting protein and the wild-type target protein may have a binding affinity that is less than the binding affinity of the wild-type targeting protein and the wild-type target protein by at least 1%, 2%, 3%, 4%, 5%, 6%, 7%, 8%, 9%, 10%, 20%, 30%, 40%, 50%, 100%, 500%, 1000%, or values therebetween.

In some implementations wherein a library of first protein binding partners is assayed against a library of second protein binding partners for binding affinity, the assay may be the yeast two-hybrid system, the AlphaSeq system, or another parallelized high-throughput library-by-library screening method. The AlphaSeq method is described in U.S. patent application Ser. No. 15/407,215, hereby incorporated herein in its entirety for all purposes.

In some implementations, the mutant species comprising the library of mutant targeting proteins or the mutant species comprising the library of mutant target proteins are selected to add steric bulk to the interface between targeting protein and target protein. The amount of space that a group of atoms occupies is called "steric bulk." Modulating the steric bulk around the interacting surface between two proteins may affect the affinity between the proteins, i.e. adding bulk to the interactive surface of one or the other of two proteins that interact may reduce affinity between the two proteins or it may increase affinity between the two proteins.

In a preferred implementation, a subset of pairs of protein binding partners that comprise one or more mutants that have been selected to introduce steric bulk, wherein binding affinity has been measured by the methods disclosed herein as higher than the binding affinity of the wild-type/wild-type protein binding partners, is further characterized. For this subset of protein binding partners, it can be inferred that the steric bulk introduced by amino acid substitution of one binding partner is filling a "hole" at the interface with the opposing binding partner. The protein-protein complex is stabilized by this hole-filling mediated by the additional bulk of the amino acid substitutions, thus increasing the affinity between the protein binding partners. In some implementations, this stabilization and enhanced affinity is mediated by new hydrogen bonds between the first protein binding partner and the second protein binding partner. This subset of protein binding partners are thus candidates for the rational design of small molecules to similarly fill the putative hole identified by the methods disclosed herein. A small molecule may be identified or designed to similarly fill the hole identified in the surface of one binding partner and stabilize the complex of the two protein binding partners and thus enhance the affinity between the two protein binding partners.

In some implementations, pairs of protein binding partners identified by the methods disclosed herein are further characterized by, e.g., crystallography, cryo-electron microscopy, micro-electron diffraction, mass spectrometry, computational modeling, among other methods for characterizing protein-protein complexes that are well known in the art. Pairs of protein binding partners or mutant protein binding partners may be further characterized individually or in the context of a protein-protein complex between the two partners.

For protein binding partners identified by the methods disclosed herein, small molecule drug candidates that recapitulate the putative hole-filling and similarly stabilize the complex between the protein binding partners may be designed or identified and screened for functional effect. Small molecule design or identification may be aided by computational modeling, computational predictions, surface modeling, cavity detection software, or computational tools e.g., Relibase, sc-PDB, Pocketome, CavBase, RAPMAD, IsoMIF, TrixP, among other protein modeling tools well known in the art. Candidate small molecules may be screened by any conventional small molecule screening platform.

In some implementations, the first binding partner and second protein binding partner are full-length proteins. In other implementations, the first binding partner and second protein binding partner are truncated proteins. In other implementations, the first binding partner and second protein binding partner are fusion proteins. In other implementations, the first binding partner and second protein binding partner are tagged proteins. Tagged proteins include proteins that are epitope tagged, e.g., FLAG-tagged, HA-tagged, His-tagged, Myc-tagged, among others known in the art. In some implementations, the first protein binding partner is a full-length protein and the second protein binding partner is a truncated protein. The first protein binding partner and second protein binding partner may each be any of the following: a full-length protein, truncated protein, fusion protein, tagged protein, or combinations thereof.

In some implementations, the first binding partner is an E3 ubiquitin ligase. In other implementations the library of first binding partners is a library of E3 ubiquitin ligases or a library of E3 ubiquitin ligase mutants generated by site saturation mutagenesis, among other methods. E3 ubiquitin ligases include MDM2, CRL4$^{CRBN}$, SCF$^{\beta-TrCP}$, UBE3A, and many other species that are well known in the art. E3 ubiquitin ligases recruit the E2 ubiquitin-conjugating enzyme that has been loaded with ubiquitin, recognize its target protein substrate, and catalyze the transfer of ubiquitin molecules from the E2 to the protein substrate for subsequent degradation by the proteasome complex.

In some implementations, the second binding partner is a target protein comprising a degron. In other implementations the library of second binding partners is a library of proteins comprising degrons or a library of proteins comprising degron mutants generated by site saturation mutagenesis, among other methods. A degron is a portion of a protein that mediates regulated protein degradation, in some cases by the ubiquitin proteasome system. Degrons may include short amino acid motifs; post-translational modifications, e.g., phosphorylation; structural motifs; sugar modifications; among others.

In some implementations wherein the second binding partner is a degron, the degron may be fluorescently tagged, i.e., by expressing the degron as a fusion protein that includes a genetically encoded fluorescent tag, e.g., green fluorescent protein (GFP), red fluorescent protein (RFP), mCherry, M Scarlet, tdTomato, among others.

In some implementations, nucleic acid vectors bearing expression cassettes encoding fluorescently tagged degrons may be transfected into mammalian cells by any number of conventional transfection methods. The nucleic acid vectors may also comprise one or more molecular barcodes, one or more selectable markers, one or more recombination sites, among other features that are commonly carried by expression vectors in mammalian cells. The fluorescently tagged degron peptides may comprise a library of degron peptides that have been modified by SSM with amino acid substitutions that contribute steric bulk to the peptide. The mammalian cells that have been transfected with the expression cassettes encoding fluorescently tagged degron peptides may be sorted by fluorescence activated cell sorting (FACS) into two or more distinct populations, for example, a first population comprising mammalian cells displaying high fluorescence intensity and a second population comprising mammalian cells displaying low fluorescence intensity. In some implementations the population comprising mammalian cells displaying low fluorescence intensity further comprises cells in which the fluorescently tagged degron peptide has been degraded by interaction with one or more E3 ubiquitin ligases that was present in the mammalian cell.

In some implementations, the expression cassettes encoding fluorescently tagged degrons may be isolated from the population of mammalian cells displaying low fluorescence intensity by any number of conventional nucleic acid extraction techniques. Expression cassettes encoding fluorescently tagged degron peptides may be sequenced by any number of nucleic acid sequencing methods to identify the degron mutants that were degraded.

In some implementations, mutant degron peptides that are identified by NGS as disclosed above may be used as "bait" in peptide pull-down assay to identify the one or more E3 ubiquitin ligases with which the mutant degron proteins interact. Complexes comprising a mutant degron peptide and the E3 ubiquitin ligases with which it interacts may be further characterized by, e.g., crystallography, cryo-electron microscopy, micro-electron diffraction, mass spectrometry, or computational modeling, among other methods for characterizing protein-protein complexes that are well known in the art.

FIG. 1 illustrates a series of charts showing the library-by-library screening capacity of the AlphaSeq method. Chart 100 illustrates screening the interaction of a first library of 100 binding partners against a second library of 100 binding partners and measuring 10,000 interactions. The first library of protein binding partners may comprise, for example, polypeptide E3 ubiquitin ligase species. The first library of protein binding partners may further comprise, for example, full-length E3 ubiquitin ligases with mapped domains; high-throughput user-designed oligo-encodable truncated E3 ubiquitin ligase domains; or polypeptide E3 ubiquitin ligase species that have been modified by site saturation mutagenesis. The second library of protein binding partners may comprise, for example, polypeptide substrate species. The second library of protein binding partners may further comprise, for example, previously known full-length mapped E3 ubiquitin ligase substrate domains; high-throughput oligo-encodable truncated E3 ubiquitin ligase substrates; E3 ubiquitin ligase substrate species that have been modified by site saturation mutagenesis; previously defined degron motifs; or computationally-predicted degron motifs. Chart 102 illustrates screening the interaction of a first library of 1,000 binding partners against a second library of 1,000 binding partners and measuring 1,000,000 interactions. Chart 104 illustrates screening the interaction of a first library of 10,000 binding partners against a second library of 10,000 binding partners and measuring 100,000,000 interactions. Chart 106 demonstrates the correlation between protein-protein affinity ($K_D$) with AlphaSeq intensity for 10,000 interactions. Chart 108 demonstrates the correlation between protein-protein affinity ($K_D$) with AlphaSeq intensity for 1,000,000 interactions. Chart 110 demonstrates the correlation between protein-protein affinity ($K_D$) with AlphaSeq intensity for 100,000,000 interactions.

Figure 2A:
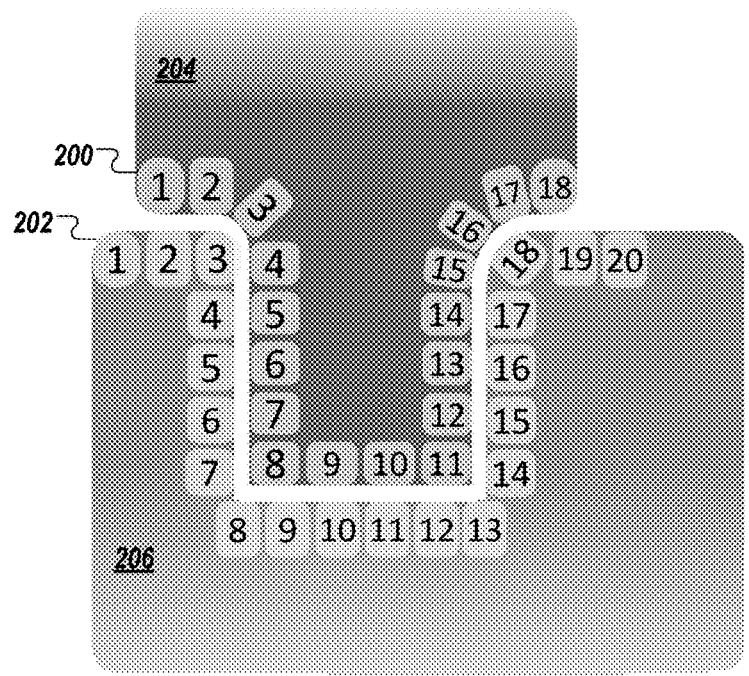
FIG. 2A is a schematic of two protein binding partners interacting in a complex, highlighting the interface between the two protein binding partners and a site saturation mutagenesis (SSM) screen of the two protein binding partners.
Figure 2B:
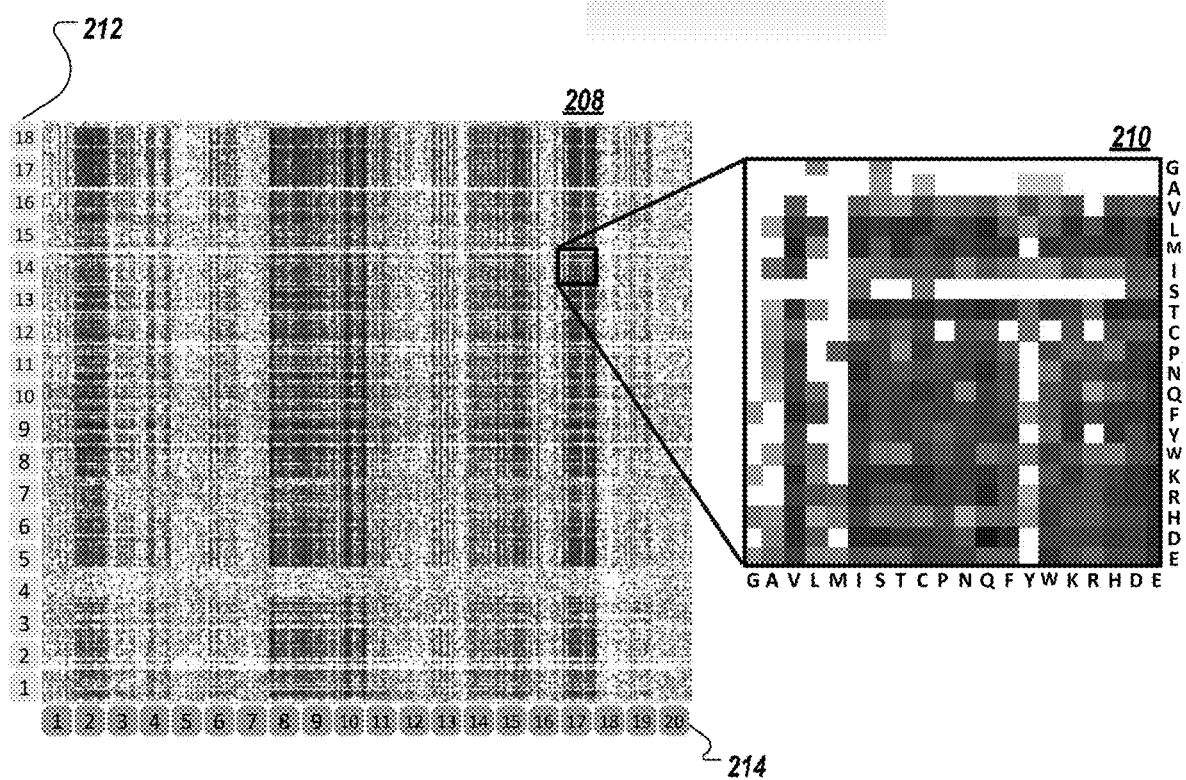
FIG. 2B is a heatmap representing the relative intensity data generated by the methods disclosed herein for a library-by-library screen of interactions between SSM libraries of two protein binding partners.

FIG. 2A is a schematic of two protein binding partners interacting in complex, emphasizing the interface between the two protein binding partners and a site saturation mutagenesis (SSM) screen of the two protein binding partners 204 and 206. Amino acid residue 200 of protein binding partner 204 corresponds to amino acid residue 202 of protein binding partner 206 Amino acid residue 200 of protein binding partner 204 may be substituted by one of any of the additional amino acid residues available, naturally occurring or artificial, and screened for interaction against a similar library of substitutions of amino acid residue 202 of protein binding partner 206. The results of such a library-by-library SSM screen are shown in FIG. 2B. Heatmap 208 illustrates the library-by-library intensity measurements by AlphaSeq of the interactions between protein binding partners carrying SSM mutations at every amino acid residue defining the protein-protein interface. Darker shades represent higher AlphaSeq intensity and lighter shades represent lower AlphaSeq intensity. For example, inset 210 highlights the library-by-library AlphaSeq intensities for an SSM library of substitutions of amino acid 212 measured against an SSM library of substitutions of amino acid 214.

Figures 3A, 3B, 3C:
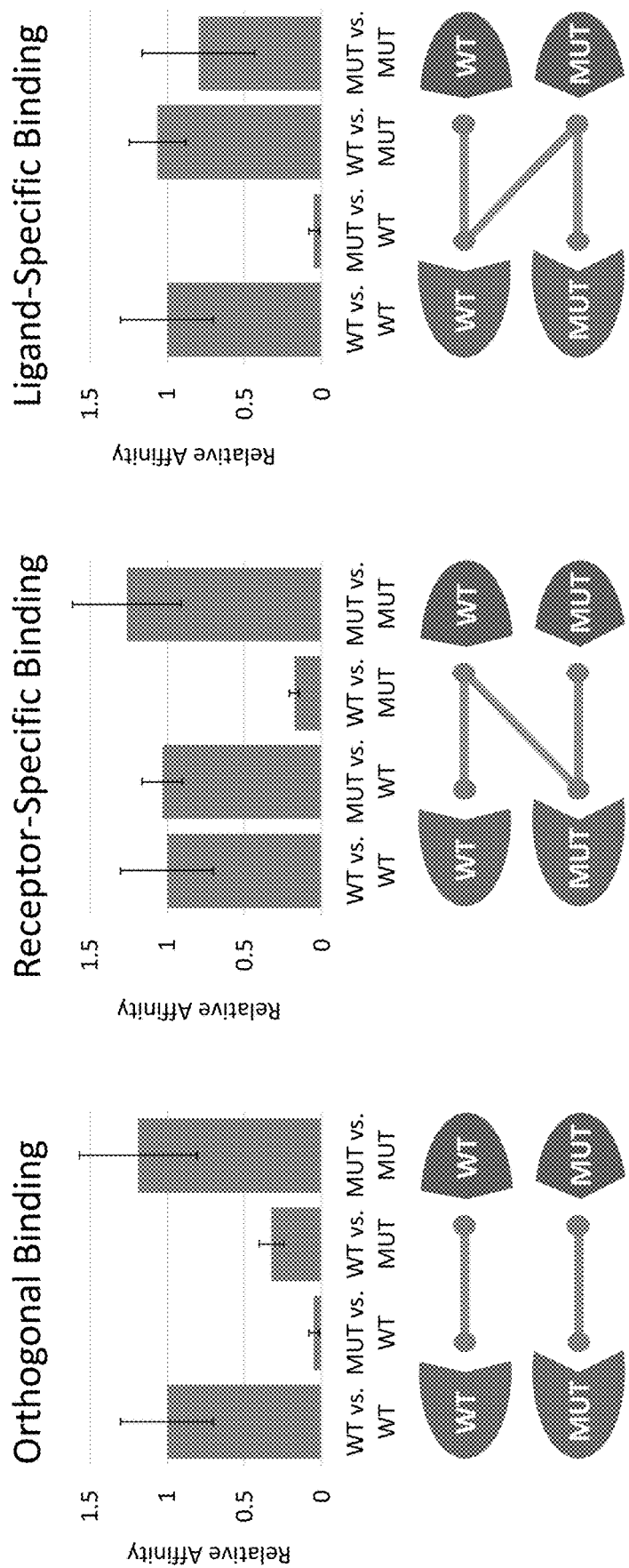
FIG. 3A is a graphical representation of quantitative interaction data for a subset of protein-protein interactions presented in the heatmap of FIG. 2B and illustrates a scenario wherein wild-type protein binding partners interact with high affinity, mutant protein binding partners interact with high affinity, but a mutant of either the first or second protein binding partner does not interact with the wild-type form of the other protein binding partner.
FIG. 3B is a graphical representation of quantitative interaction data for a subset of protein-protein interactions presented in the heatmap of FIG. 2B and illustrates a scenario wherein both the wild-type and mutant form of the first protein binding partner interact with the wild-type form of the second protein binding partner, but the wild-type first protein binding partner does not interact with the mutant second protein binding partner, i.e., mutation of the second protein binding partner abolishes interaction with the wild-type first protein binding partner.
FIG. 3C is a graphical representation of quantitative interaction data for a subset of protein-protein interactions presented in the heatmap of FIG. 2B and illustrates a scenario wherein both the wild-type and mutant form of the first protein binding partner interact with the mutant form of the second protein binding partner, but the mutant first protein binding partner does not interact with the wild-type second protein binding partner, i.e., mutation of the first protein binding partner abolishes interaction with the wild-type second protein binding partner.

FIGS. 3A-3C are graphical representations of a subset of protein-protein interactions detected by the data presented in FIGS. 2A-2B and illustrate the capability of the methods disclosed herein to detect relative affinity between wild-type and mutant protein binding partners and the effect of single amino acid substitutions on affinity between two protein binding partners. FIG. 3A illustrates a scenario wherein wild-type protein binding partners interact with high affinity, mutant protein binding partners interact with high affinity, but a mutant of either the first or second protein binding partner does not interact with the wild-type form of the other protein binding partner. FIG. 3B illustrates a scenario wherein both the wild-type and mutant form of the first protein binding partner interact with the wild-type form of the second protein binding partner, but the wild-type first protein binding partner does not interact with the mutant second protein binding partner, i.e., mutation of the second protein binding partner abolishes interaction with the wild-type first protein binding partner. FIG. 3C illustrates a scenario wherein both the wild-type and mutant form of the first protein binding partner interact with the mutant form of the second protein binding partner, but the mutant first protein binding partner does not interact with the wild-type second protein binding partner, i.e., mutation of the first protein binding partner abolishes interaction with the wild-type second protein binding partner.

Figure 4:
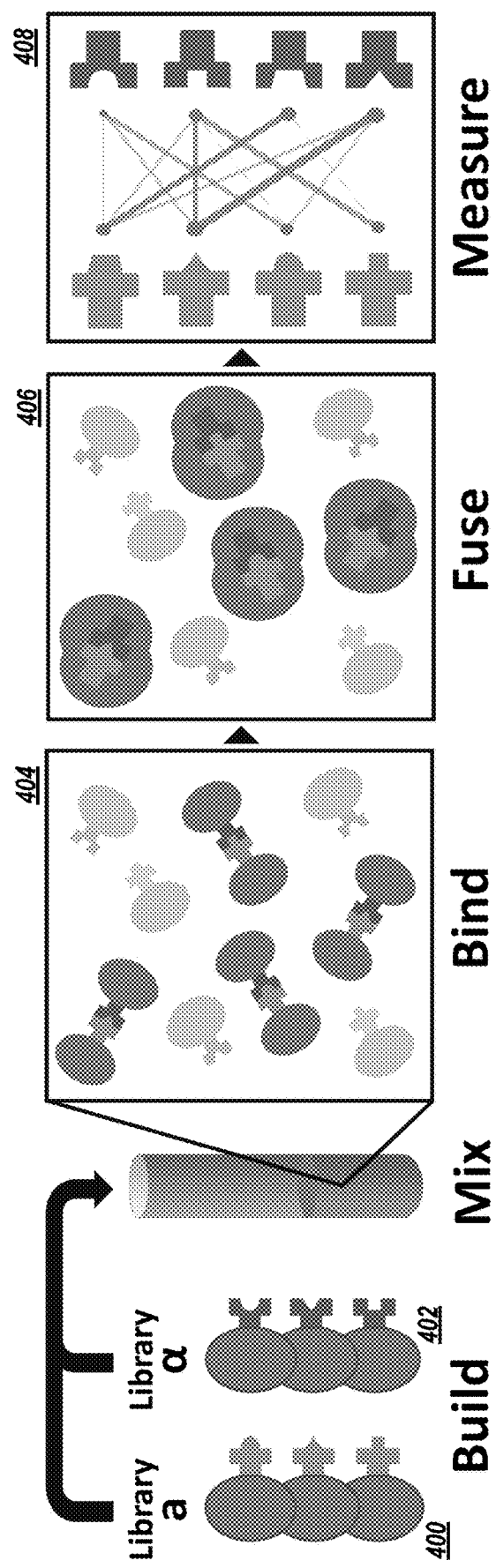
FIG. 4 illustrates the workflow of a library-by-library protein-protein interaction screen using the methods disclosed herein.

FIG. 4 illustrates the workflow of a library-by-library protein-protein interaction screen using AlphaSeq. A first library 400 of protein binding partners and second library 402 of protein binding partners are generated by site-saturation mutagenesis and expressed in yeast. The two library populations are mixed and protein binding partners bind in interaction step 404. Cells expressing protein binding partners that have interacted mate in fusing step 406. Protein-protein interactions between the first and second libraries are detected and quantified in measuring step 408.

Figure 5:
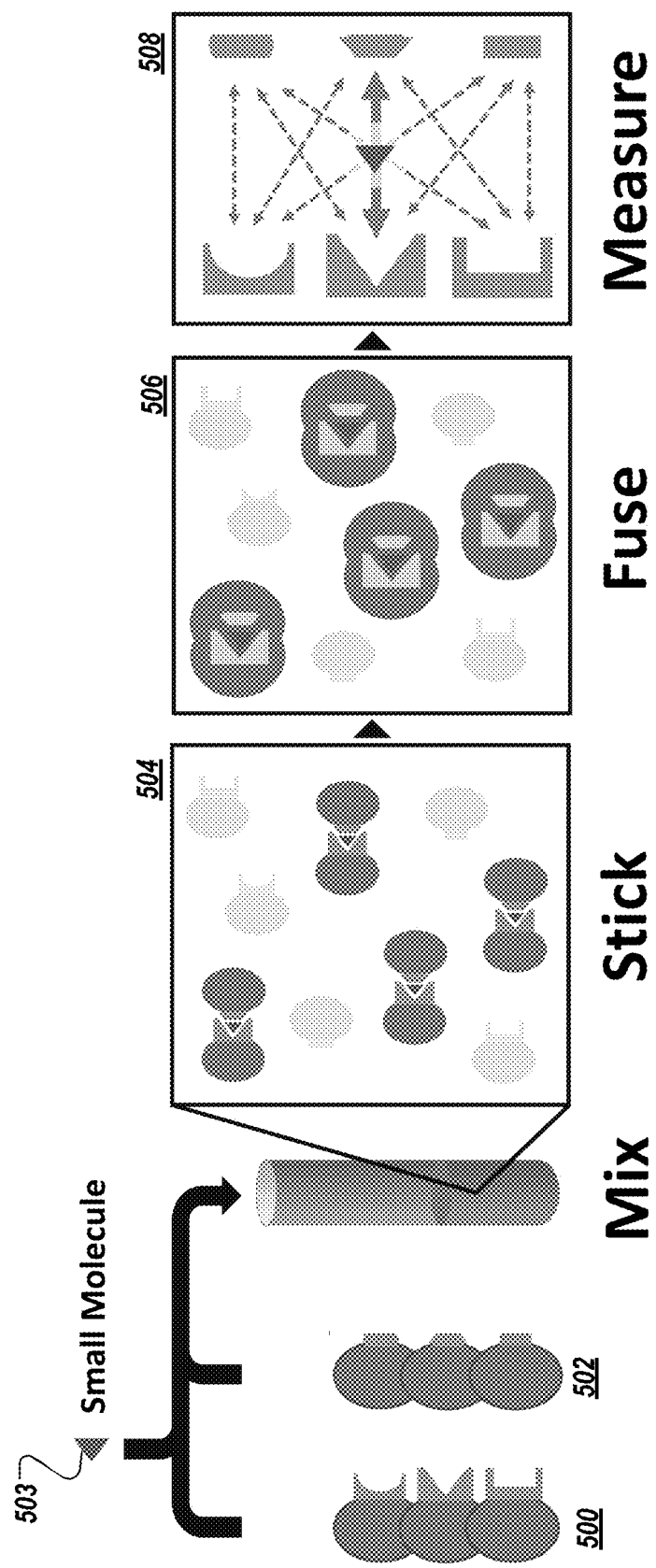
FIG. 5 illustrates the workflow of a library-by-library protein-protein interaction screen in the presence of a candidate small molecule using the methods disclosed herein.

FIG. 5 illustrates the workflow of a library-by-library protein-protein interaction screen in the presence of a candidate small molecule using AlphaSeq. A first library 500 of protein binding partners and second library 502 of protein binding partners are generated by site-saturation mutagenesis and expressed in yeast. The two library populations are mixed in liquid culture, small molecule 503 is introduced to the culture, and protein binding partners bind in interaction step 504. Cells expressing protein binding partners that have interacted mate in fusing step 506. Protein-protein interactions between the first and second libraries are detected and quantified in measuring step 508.

Figure 6B:
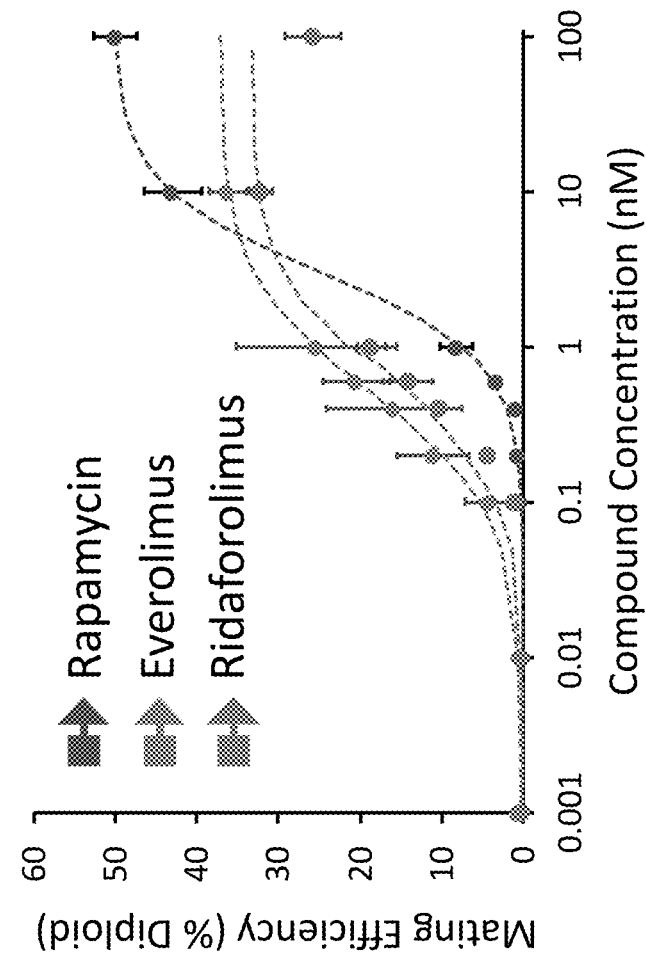
FIG. 6B is a plot depicting the agonistic effect of rapamycin and its analogs on the interaction between FKBP12 and the FRB domain as detected by the methods disclosed herein.
Figure 6A:
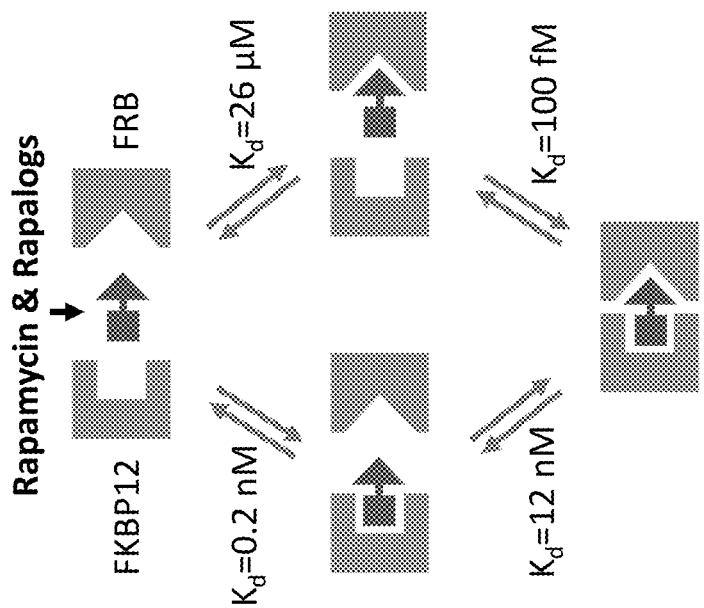
FIG. 6A illustrates the capability of the methods disclosed herein to detect the effect of known small molecule agonists on the interaction between two protein binding partners.

FIGS. 6A and 6B demonstrate the capability of AlphaSeq to detect the effect of known small molecule agonists on the interaction between two protein binding partners. FIG. 6A illustrates the known dissociation constants between the prolyl isomerase FKBP12, the FRB domain of TOR, and the small molecule rapamycin and its analogs everolimus and ridaforolimus. Accordingly, FIG. 6B is a chart illustrating the agonistic effect of rapamycin and its analogs on the interaction between FKBP12 and the FRB domain. Increasing compound concentration correlates with increasing mating efficiency, and thus, increased binding affinity between the two protein binding partners.

Figure 7A:
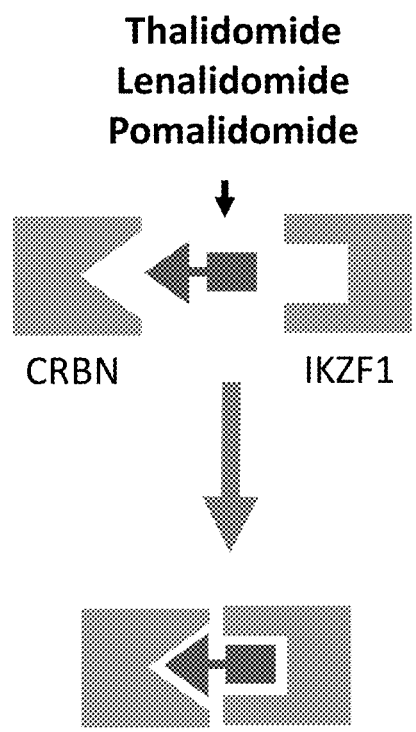
FIG. 7A is a schematic illustrating thalidomide, or its analogs, mediating the interaction between CRBN and IKZF1.
Figure 7B:
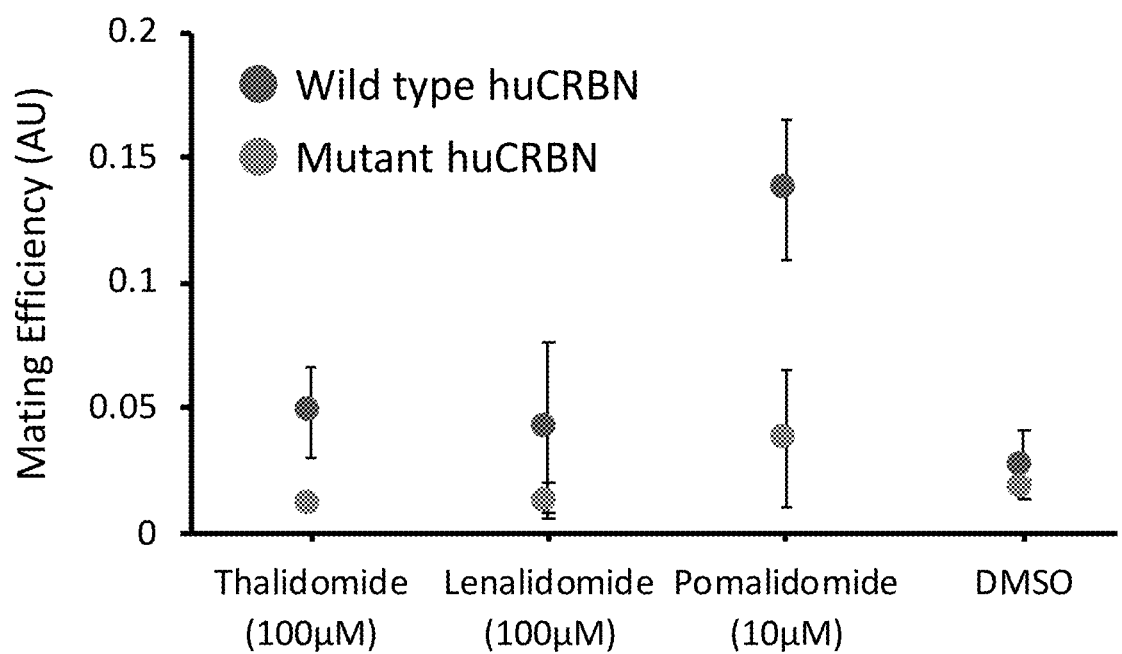
FIG. 7B is a chart highlighting the agonistic effect of thalidomide, lenalidomide, and pomalidomide on the interaction of IKZF1 with wild-type CRBN, but not mutant CRBN.

FIGS. 7A and 7B demonstrate the capability of AlphaSeq in detecting the known agonistic effect of thalidomide and its analogs on the interaction between the E3 ubiquitin ligase Cereblon (CRBN) and its substrate Ikaros factor 1 (IKZF1). FIG. 7A is a schematic illustrating thalidomide, or its analogs, mediating the interaction between CRBN and IKZF1. FIG. 7B is a chart highlighting the agonistic effect of thalidomide, lenalidomide, and pomalidomide on the interaction of IKZF1 with wild-type CRBN, but not mutant CRBN.

Figure 8:
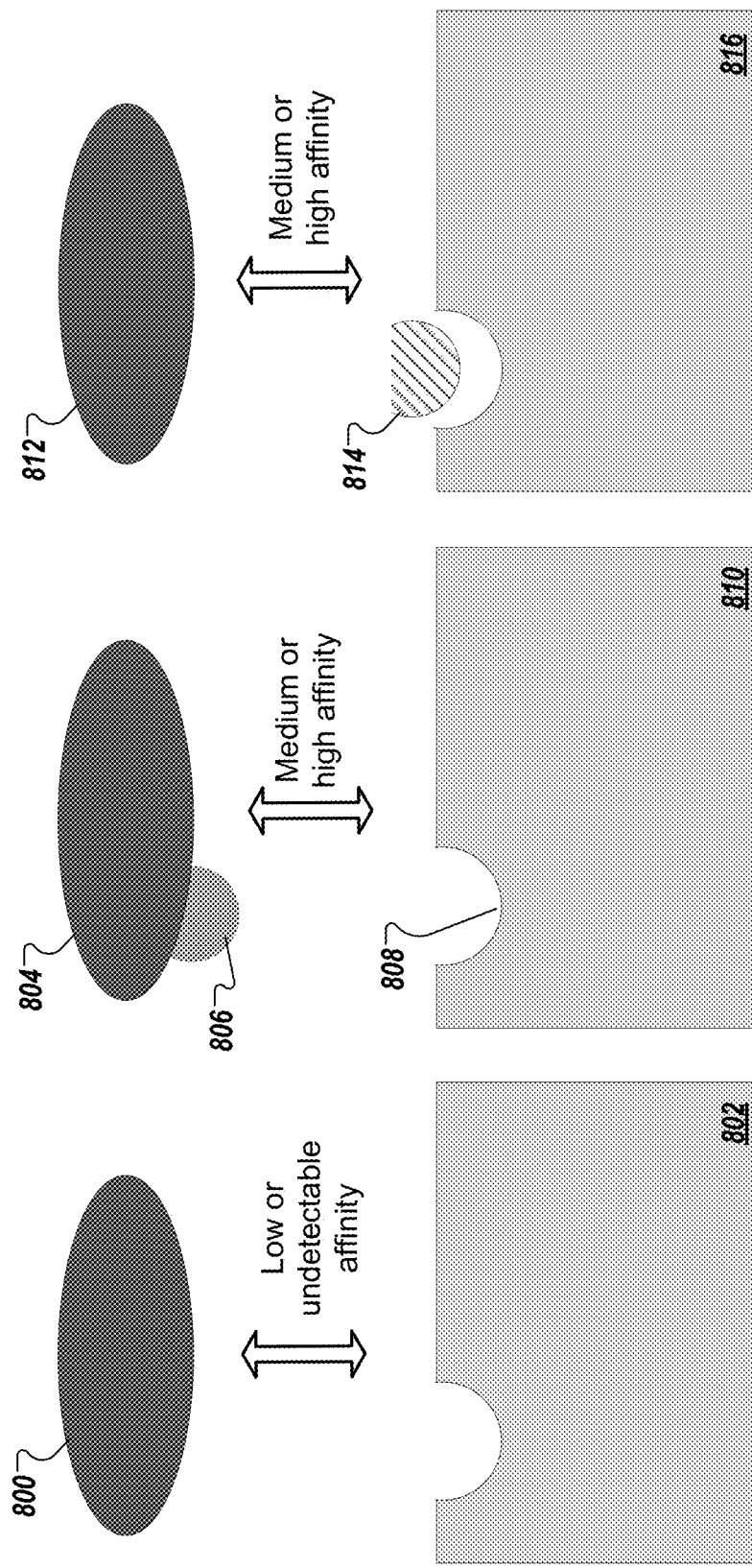
FIG. 8 is a schematic illustrating the process according to the methods disclosed herein for identifying putative "holes" in a protein binding partner that may indicate candidates for functional small molecule screening.

FIG. 8 is a schematic illustrating the process for identifying putative "holes" in a protein binding partner that may indicate candidates for functional small molecule screening. Wild-type protein binding partner 800 and wild-type protein binding partner 802, for example, may have weak interaction and low or undetectable affinity. Protein binding partner 804 has been modified by SSM with amino acid substitutions that contribute steric bulk 806. Protein binding partners 804 and 810 show dramatically increased affinity with a very low $K_D$, suggesting the presence of putative "hole" 808. Additional steric bulk 806 is filling "hole" 808 and stabilizing the ternary complex between protein binding partners 804 and 810. Similarly, small molecule 814 may be identified or designed to fill the putative hole, stabilize the ternary complex, and enhance affinity between protein binding partners 812 and 816.

Figure 9:
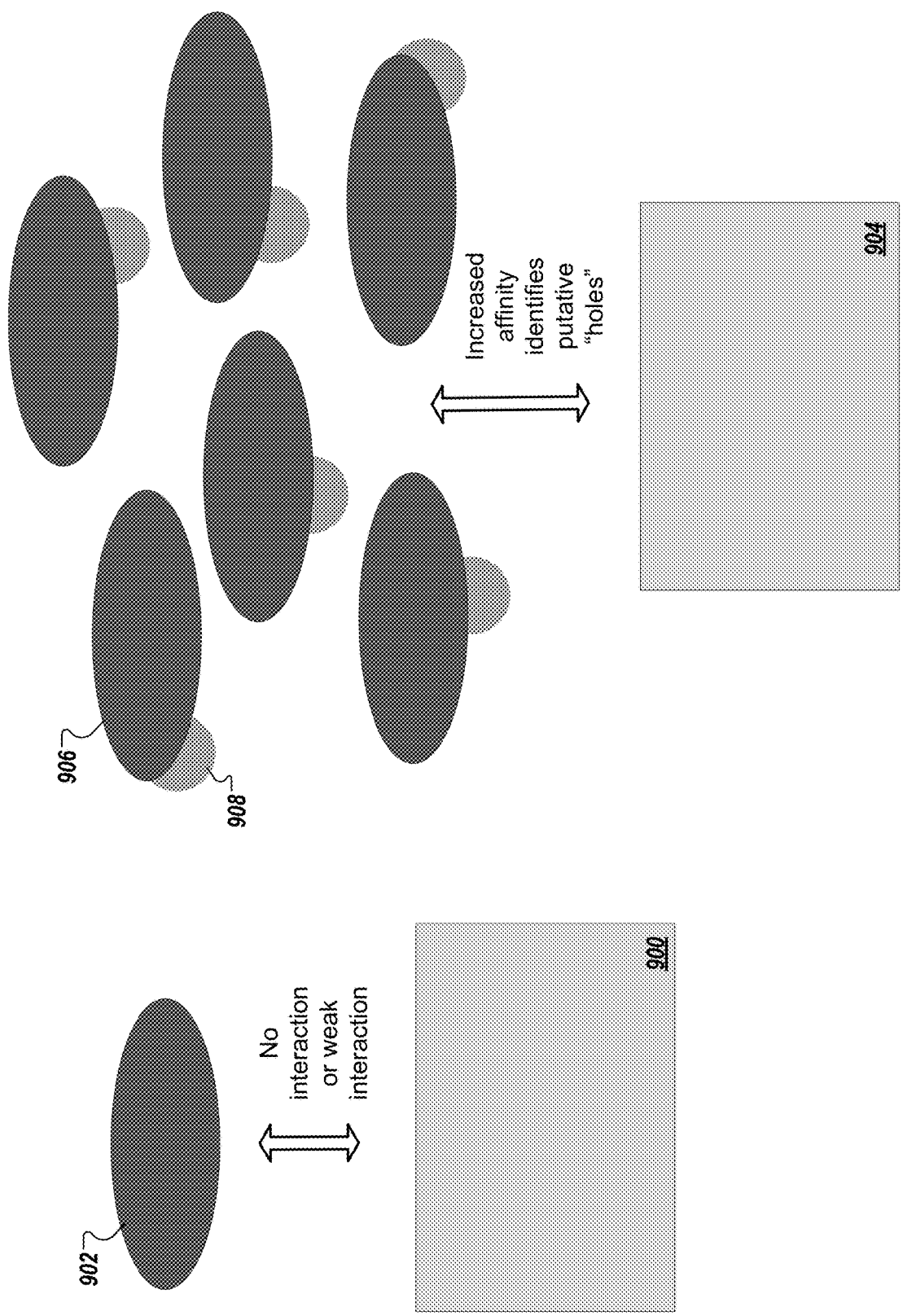
FIG. 9 is a schematic illustrating a screen for interaction between a first protein binding partner and a library of second protein binding partners according to the methods disclosed herein.

FIG. 9 is a schematic illustrating a screen for interaction between a first protein binding partner and a library of second protein binding partners. Wild-type protein binding partner 900 and wild-type protein binding partner 902 show little or no binding affinity. Protein binding partner 906 has been modified by SSM with amino acid substitutions that contribute steric bulk 908 and is a member of a library of protein binding partners that have been similarly modified by SSM, each carrying different amino acid substitutions that contribute additional steric bulk. This library of mutant protein binding partners is screened against protein binding partner 904 to detect and measure binding affinity and identify putative "holes" that represent druggable targets for small molecule development. Alternatively, protein binding partner 904 may be modified by SSM with amino acid substitutions that contribute steric bulk to generate a library of protein binding partners that have been similarly modified by SSM, and this library may be screened against protein binding partner 906.

Figure 10:
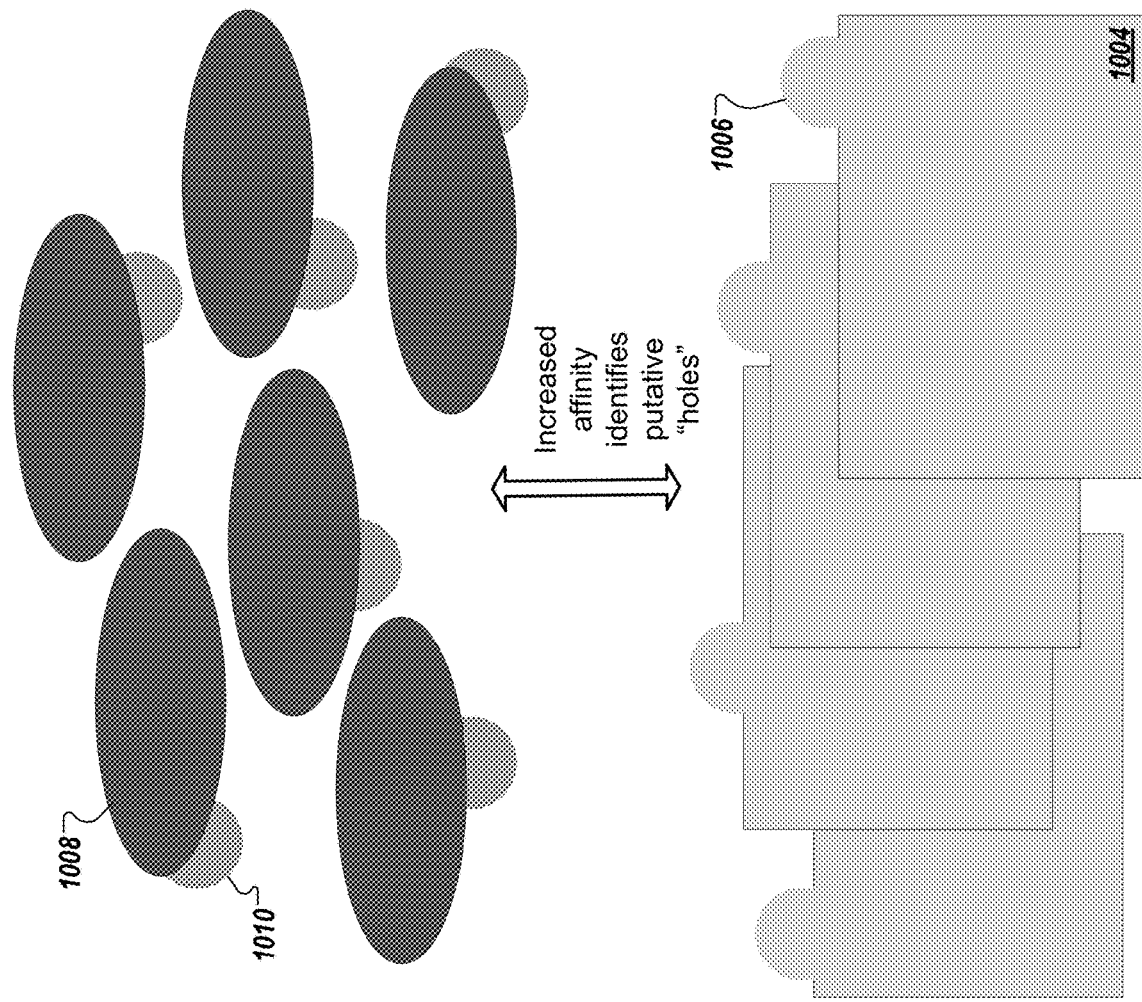
FIG. 10 is a schematic illustrating a screen for interaction between a library of first protein binding partners and a library of second protein binding partners.
Figure 10:
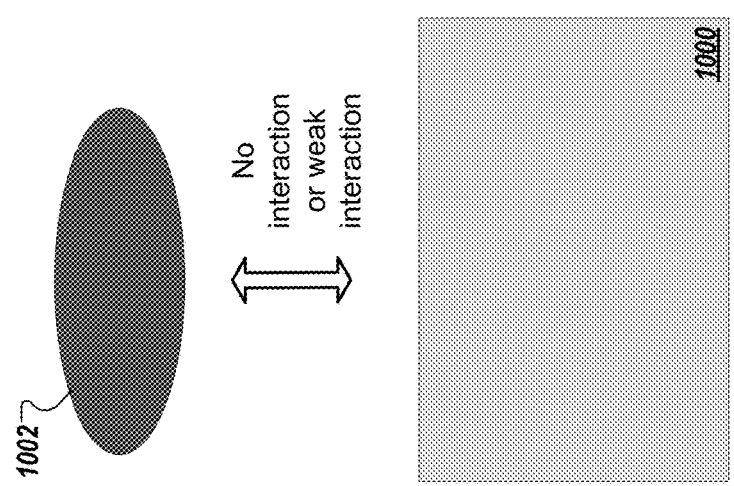

FIG. 10 is a schematic illustrating a screen for interaction between a library of first protein binding partner and a library of second protein binding partners. Wild-type protein binding partner 1000 and wild-type protein binding partner 1002 show little or no binding affinity. Protein binding partner 1004 has been modified by SSM with amino acid substitutions that contribute steric bulk 1006 and is a member of a library of protein binding partners that have been similarly modified by SSM, each carrying different amino acid substitutions that contribute additional steric bulk. Protein binding partner 1008 has been modified by SSM with amino acid substitutions that contribute steric bulk 1010 and is a member of a library of protein binding partners that have been similarly modified by SSM, each carrying different amino acid substitutions that contribute additional steric bulk. The library of mutant protein binding partners comprising mutant protein binding partner 1004 is screened against the library of mutant protein binding partners comprising mutant protein binding partner 1008 to detect and measure binding affinity and identify putative "holes" that represent druggable targets for small molecule development.

Figure 11:
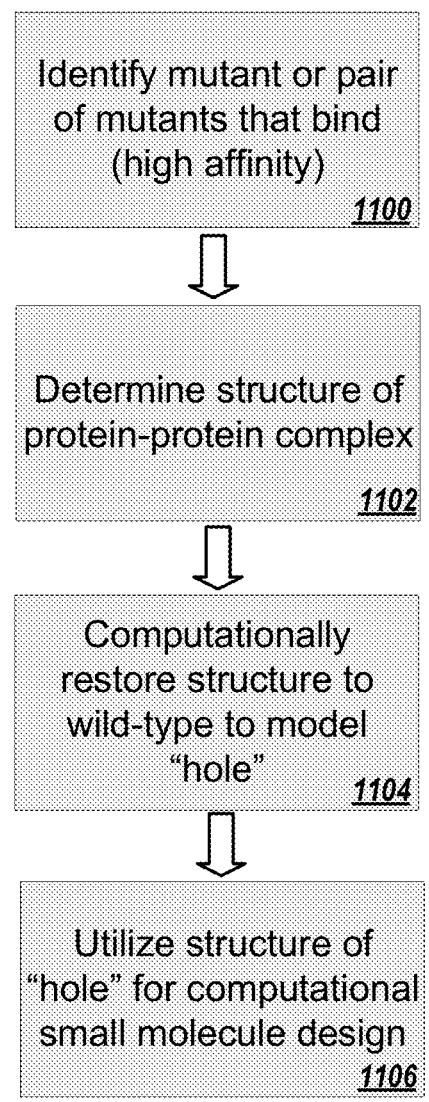
FIG. 11 is a flowchart illustrating the workflow of the methods disclosed herein.

FIG. 11 is a flowchart illustrating the workflow of the methods disclosed herein. In step 1100, according to the methods disclosed herein, pairs of protein binding partners wherein one or both protein binding partners have been mutated to introduce steric bulk, and that bind with increased affinity relative to the wild-type protein binding partners, are identified. In step 1102, the mutant protein binding partners are further characterized by, for example, crystallography to determine their structure either in complex or individually. In step 1104, the resulting structures are computationally restored to their wild-type amino acid sequence. Comparison between the mutants identified in step 1100 and their respective wild-type structure indicates the structures of putative "holes." In step 1106, the structures of putative holes are used for computational small molecule design.

Figure 12:
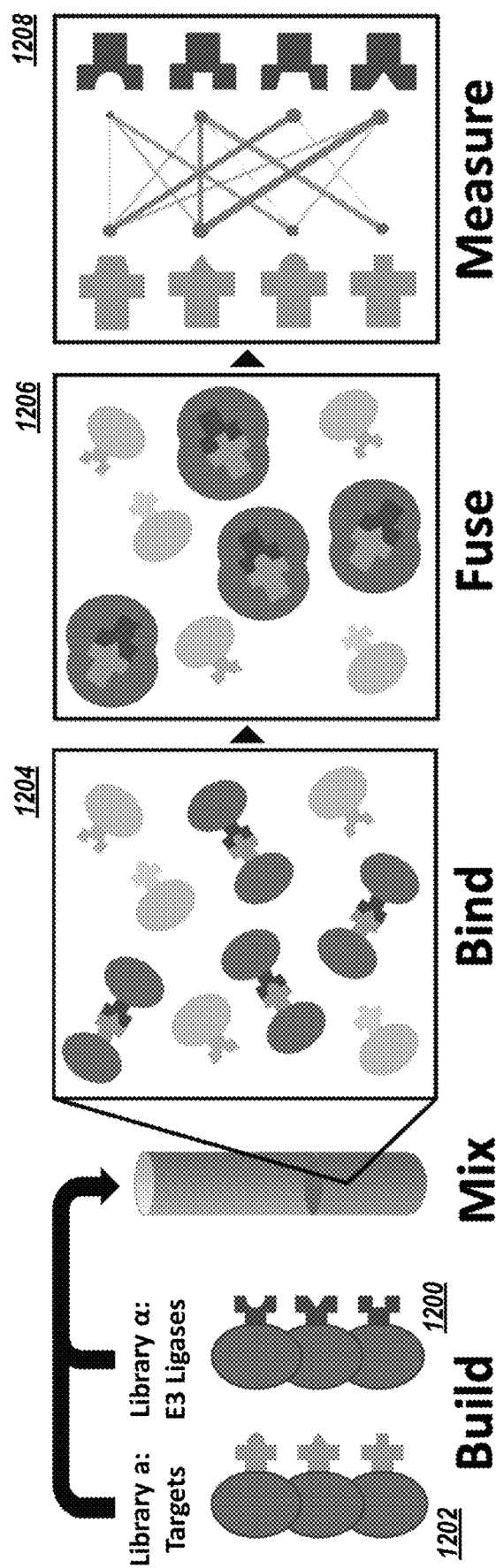
FIG. 12 illustrates the workflow of a library-by-library protein-protein interaction screen using the methods disclosed herein, wherein more than one member of the first library of protein binding partners are polypeptide E3 ubiquitin ligases and more than one member of the second library of protein binding partners are polypeptide target substrates.

FIG. 12 illustrates the workflow of a library-by-library protein-protein interaction screen using AlphaSeq, wherein more than one member of the first library of protein binding partners are polypeptide E3 ubiquitin ligases and more than one member of the second library of protein binding partners are polypeptide target substrates. A first library 1200 of E3 ubiquitin ligases and second library 1202 of polypeptide target substrates are generated by mutagenesis and expressed in yeast. The two library populations are mixed and protein binding partners bind in interaction step 1204. Cells expressing protein binding partners that have interacted mate in fusing step 1206. Protein-protein interactions between the first and second libraries are detected and quantified in measuring step 1208.

Figure 13:
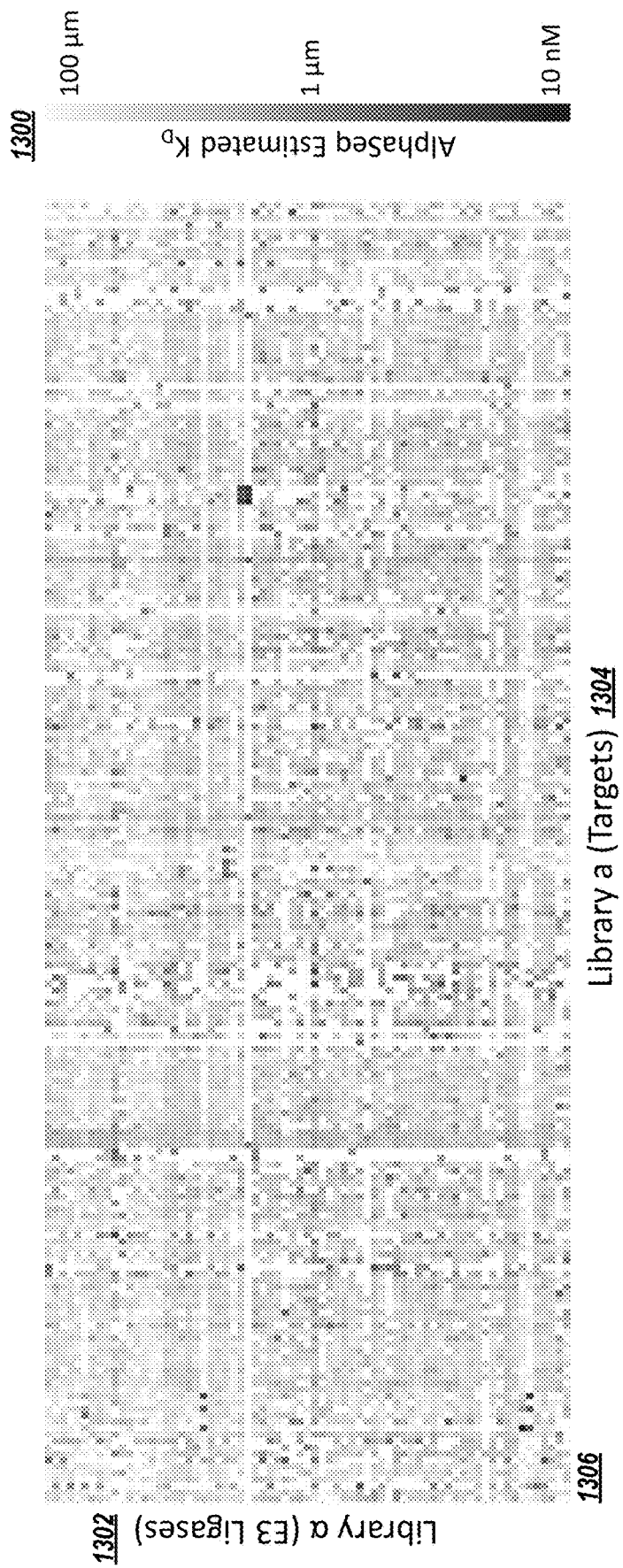
FIG. 13 illustrates a heatmap of quantitative binding affinity data generated by the methods disclosed herein representing intensities of interactions between polypeptide E3 ubiquitin ligases and polypeptide target substrates.

FIG. 13 illustrates a heatmap 1306 of AlphaSeq data representing intensities of interactions between polypeptide E3 ubiquitin ligases 1302 and polypeptide target substrates 1304, wherein darker shading indicates a relatively stronger interaction and lighter shading indicates a relatively weaker interaction, according to scale bar 1300. Individual members of the library of polypeptide E3 ubiquitin ligases 1302 represented by the vertical axis of the grid and individual members of the library of polypeptide target substrates 1304 are represented by the horizontal axis of the grid. The shaded boxes of the heatmap represent the strength of the interaction between a single member of the library of polypeptide E3 ubiquitin ligases 1302 and a single member of the library of polypeptide target substrates 1304.

Figure 14A:
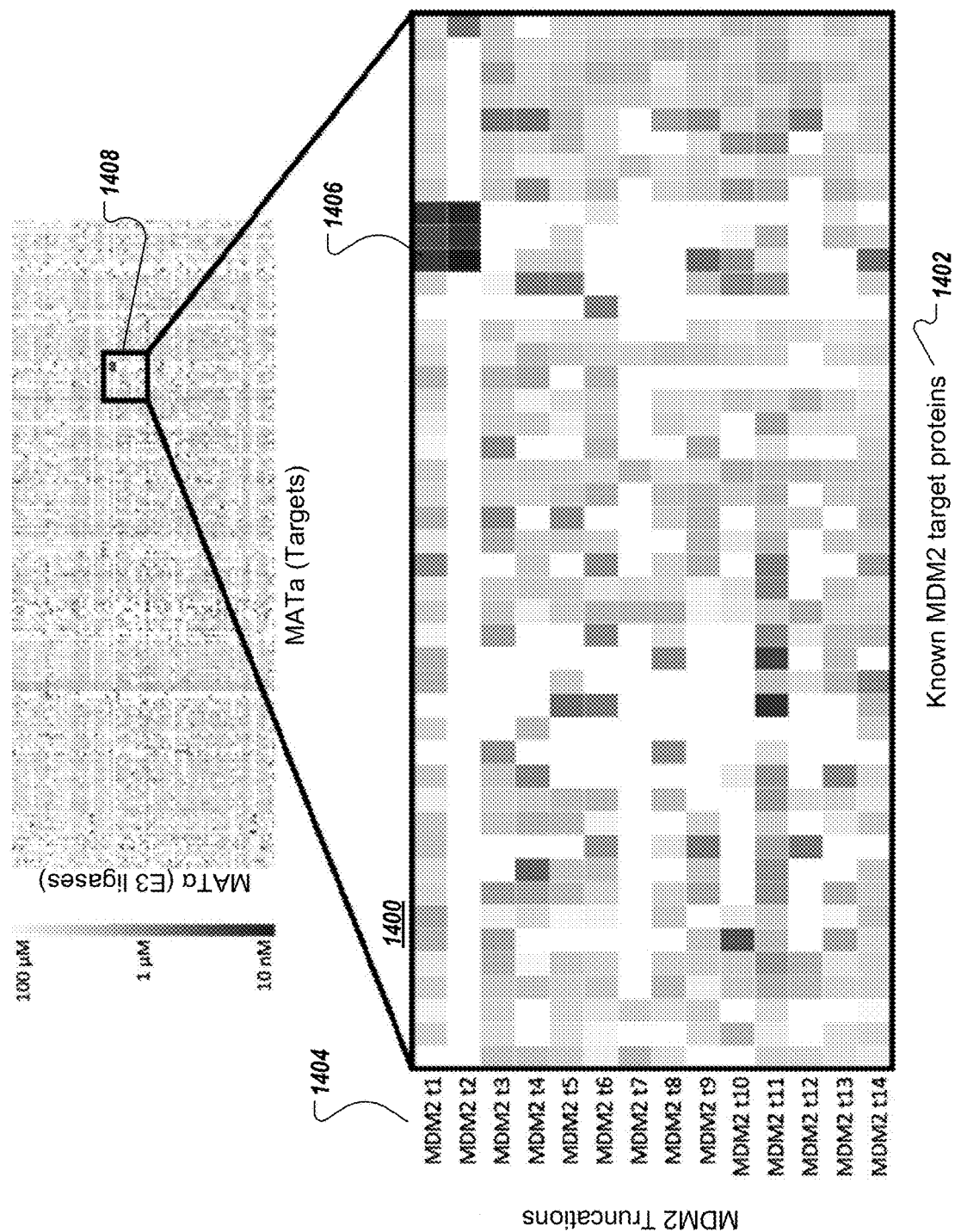
FIG. 14A illustrates a zoomed in section of heatmap of FIG. 13 highlighting intensities of particular interactions between protein binding partners in greater resolution.

FIG. 14A illustrates a zoomed in section 1400 of heatmap 1306 highlighting intensities of particular interactions between protein binding partners in greater resolution, wherein box 1408 has been selected to be examined in greater detail. The E3 ubiquitin ligase MDM2 is well-characterized and known to interact with hundreds of polypeptide target substrates. An AlphaSeq assay was performed using a library of various truncated MDM2 E3 ubiquitin ligases and library of a subset of known MDM2 target substrates. The library of truncated MDM2 E3 ubiquitin ligases are represented by the vertical axis 1404 of the heatmap 1400 and the library of known MDM2 target substrates are represented by the horizontal axis 1402 of the heatmap 1400. Darker shading, for example in the boxes in the vicinity of box 1406, indicate a relatively stronger interaction between individual members of the library of various truncated MDM2 E3 ubiquitin ligases and library of a subset of known MDM2 target substrates.

Figure 14B:
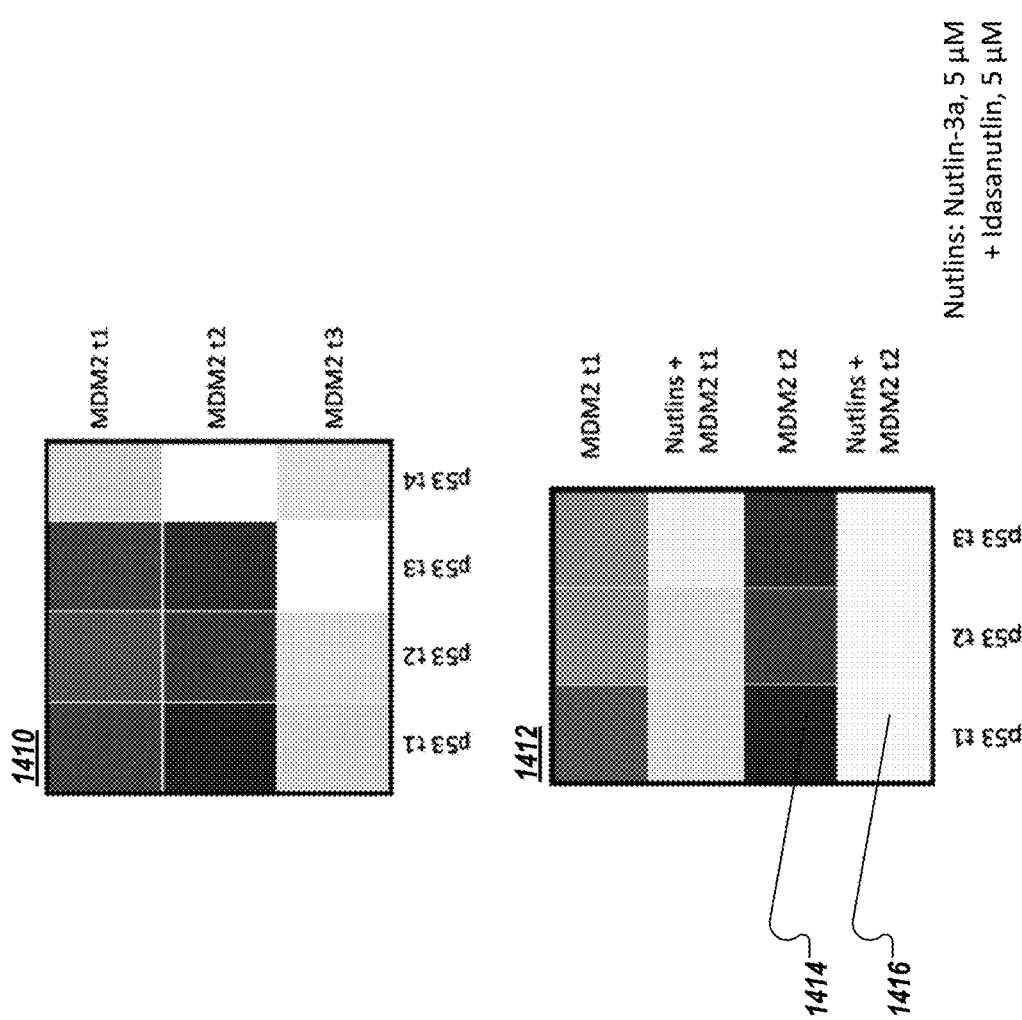
FIG. 14B illustrates a section of the heatmap of FIG. 14A zoomed in further to depict greater detail, and the results of an additional experiment including small molecule compounds.

FIG. 14B illustrates a section of heatmap 1400 zoomed in further to depict greater detail, and the results of an additional experiment including small molecule compounds. Heatmap 1410 depicts a subset of squares from heatmap 1400 in the vicinity of square 1406 indicated in FIG. 14A. Interaction between E3 ubiquitin ligase MDM2 and polypeptide target substrate p53 are well known and thoroughly characterized. Heatmap 1410 represents relative intensities of pair-wise interactions between various truncations of E3 ubiquitin ligase MDM2 (MDM2 t1; MDM2 t2; MDM2 t3) and various truncations of polypeptide target substrate p53 (p53 t1; p53 t2; p53 t3; p53 t4). Canonical interactions between individual MDM2 truncations and individual p53 truncations occur between specific truncated forms only, as reported in the literature, demonstrating that the AlphaSeq assay robustly detects and quantifies the strength of interactions between polypeptide E3 ubiquitin ligases and polypeptide target substrates. Further, heatmap 1412 is an additional experiment measuring relative intensities of pair-wise interactions between each of several MDM2 truncations and p53 truncations with and without the presence of two small molecule compounds, nutlins, which are cis-imidazoline analogs that are known to inhibit the interaction between MDM2 and p53. For example, box 1414 represents a strong interaction between MDM2 t2 and p53 t1 in the absence of nutlins. Box 1416 represents a relatively weak interaction between MDM2 t2 and p53 t1 in the presence of nutlins, due to the nutlins disrupting the interaction. This experiment further demonstrates that the AlphaSeq assay robustly detects and quantifies the strength of interactions between polypeptide E3 ubiquitin ligases and polypeptide target substrates and shows that the assay detects disruptions between protein binding partners due to the effects of small molecule compounds.

Figure 15:
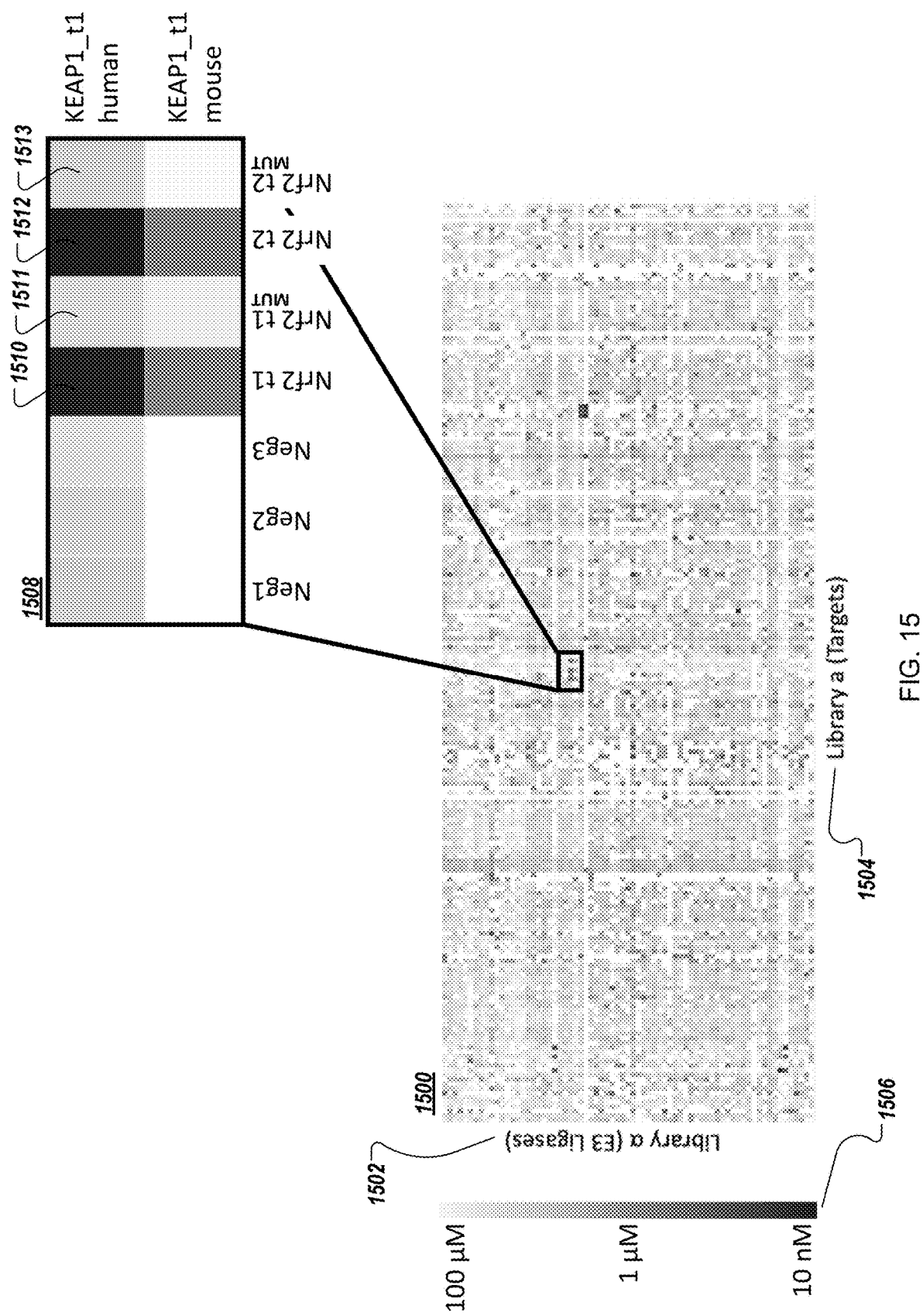
FIG. 15 illustrates a heatmap of quantitative binding affinity data generated by the methods disclosed herein between the polypeptide E3 ubiquitin ligases KEAP1 and the polypeptide target substrate Nrf2.

FIG. 15 illustrates a heatmap 1500 of AlphaSeq data representing intensities of interactions between polypeptide E3 ubiquitin ligases 1502 and polypeptide target substrates 1504, wherein darker shading indicates a relatively stronger interaction and lighter shading indicates a relatively weaker interaction, according to scale bar 1506. Individual members of the library of polypeptide E3 ubiquitin ligases 1502 are represented by the vertical axis of the grid and individual members of the library of polypeptide target substrates 1504 are represented by the horizontal axis of the grid. Heatmap 1508 depicts a subset of squares from heatmap 1500 zoomed in to highlight specific interactions in greater detail. Interaction between E3 ubiquitin ligase KEAP1 and polypeptide target substrate Nrf2 are well known and well characterized in the literature. Heatmap 1508 shows relative intensity of pairwise interactions between a truncation of human KEAP1 or mouse KEAP1 with several Nrf2 variants (Nrf2 t1; Nrf2 t1 mutant; Nrf2 t2; Nrf2 t2 mutant). Each of the Nrf2 truncation mutants were generated by targeted mutagenesis. As indicated by boxes 1510 and 1512, human KEAP1 t1 has relatively strong interaction with each of Nrf2 t1 and Nrf2 t2. However, boxes 1511 and 1513 show that mutations of each of Nrf2 t1 and Nrf2 t2 disrupt this interaction. The same is true for mouse KEAP1. This experiment demonstrates that the AlphaSeq assay robustly detects and quantifies the strength of interactions between polypeptide E3 ubiquitin ligases and polypeptide target substrates and shows that the assay may detect disruptions between protein binding partners due to the mutation of one of the protein binding partners.

Figure 16:
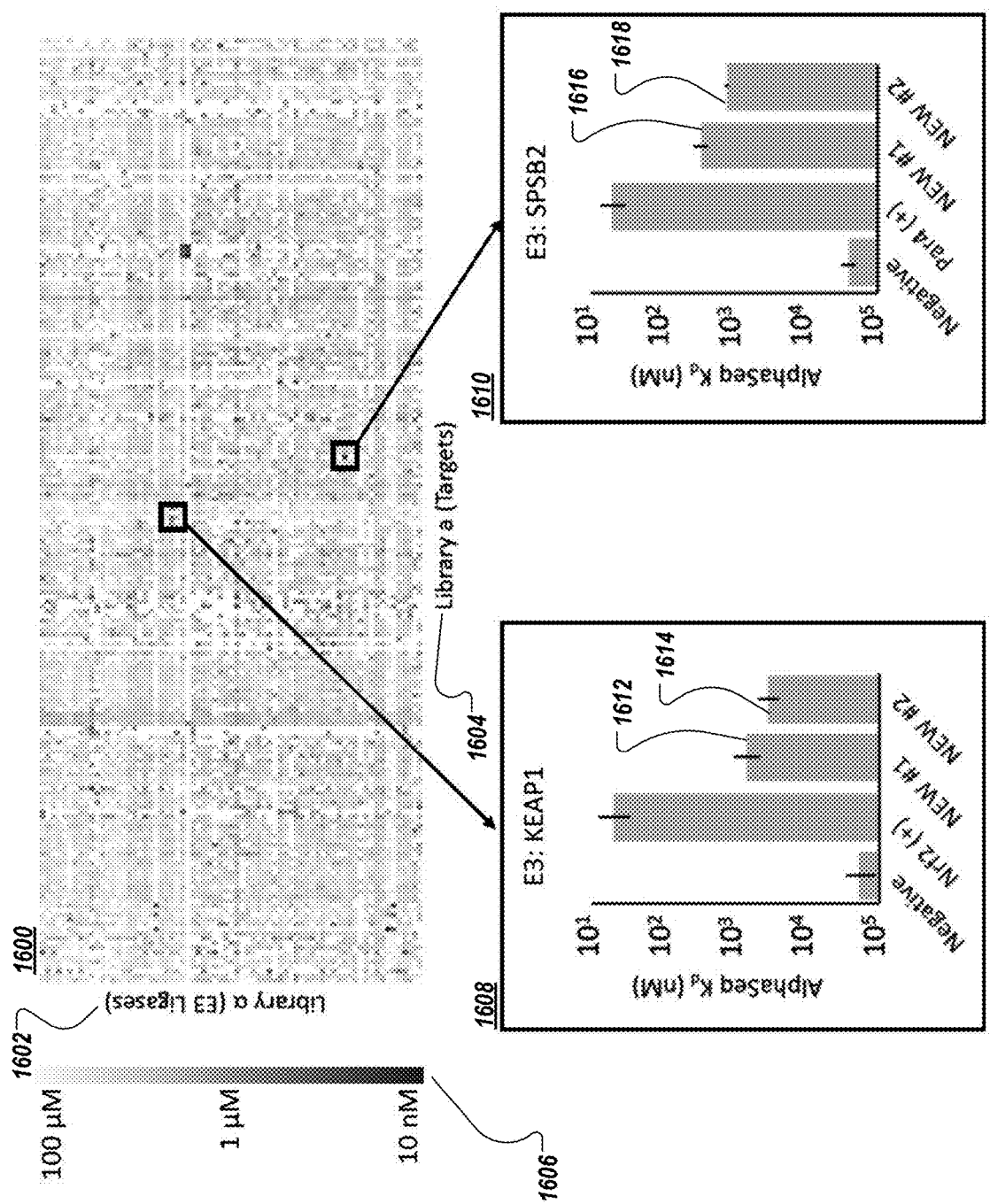
FIG. 16 illustrates a heatmap of quantitative binding affinity data representing intensities of interactions between polypeptide E3 ubiquitin ligases and polypeptide target substrates and identifies novel substrates for the E3 ubiquitin ligases KEAP1 and SPSB2.

FIG. 16 illustrates a heatmap 1600 of AlphaSeq data representing intensities of interactions between polypeptide E3 ubiquitin ligases 1602 and polypeptide target substrates 1604, wherein darker shading indicates a relatively stronger interaction and lighter shading indicates a relatively weaker interaction, according to scale bar 1606. Inset 1608 highlights quantitative data for interactions between the E3 ubiquitin ligase KEAP1 and several polypeptide target substrates. Nrf2 is a previously known target substrate for KEAP1 and the interaction intensity between KEAP1 and Nrf2 is at least three orders of magnitude higher than between KEAP1 and a negative control polypeptide target substrate. In the graph, bars 1612 and 1614 represent quantitative interaction intensity data for two novel KEAP1 substrates. These novel polypeptide target substrates have an interaction intensity with KEAP1 that is at least an order of magnitude higher than the interaction of KEAP1 with a negative control. These two putative substrates of KEAP1 represent possible targets wherein a small molecule may be selected, identified, or designed to strengthen the interaction between KEAP1 and the putative target substrate.

Inset 1610 highlights quantitative data for interactions between the E3 ubiquitin ligase SPSB2 and several polypeptide target substrates. Par4 is a previously known target substrate for SPSB2 and the interaction intensity between SPSB2 and Par4 is at least three orders of magnitude higher than between SPSB2 and a negative control polypeptide target substrate. In the graph, bars 1616 and 1618 represent quantitative interaction intensity data for two novel SPSB2 substrates. These novel polypeptide target substrates have an interaction intensity with SPSB2 that is at least an order of magnitude higher than the interaction of SPSB2 with a negative control. These two putative substrates of SPSB2 represent possible targets wherein a small molecule may be selected, identified, or designed to strengthen the interaction between SPSB2 and the putative target substrate. This experiment demonstrates that the AlphaSeq assay robustly detects and quantifies the strength of interactions between polypeptide E3 ubiquitin ligases and polypeptide target substrates and shows that the assay may detect novel interactions between protein binding partners, novel interactions that may be candidates for small molecule discovery.

Figure 17A:
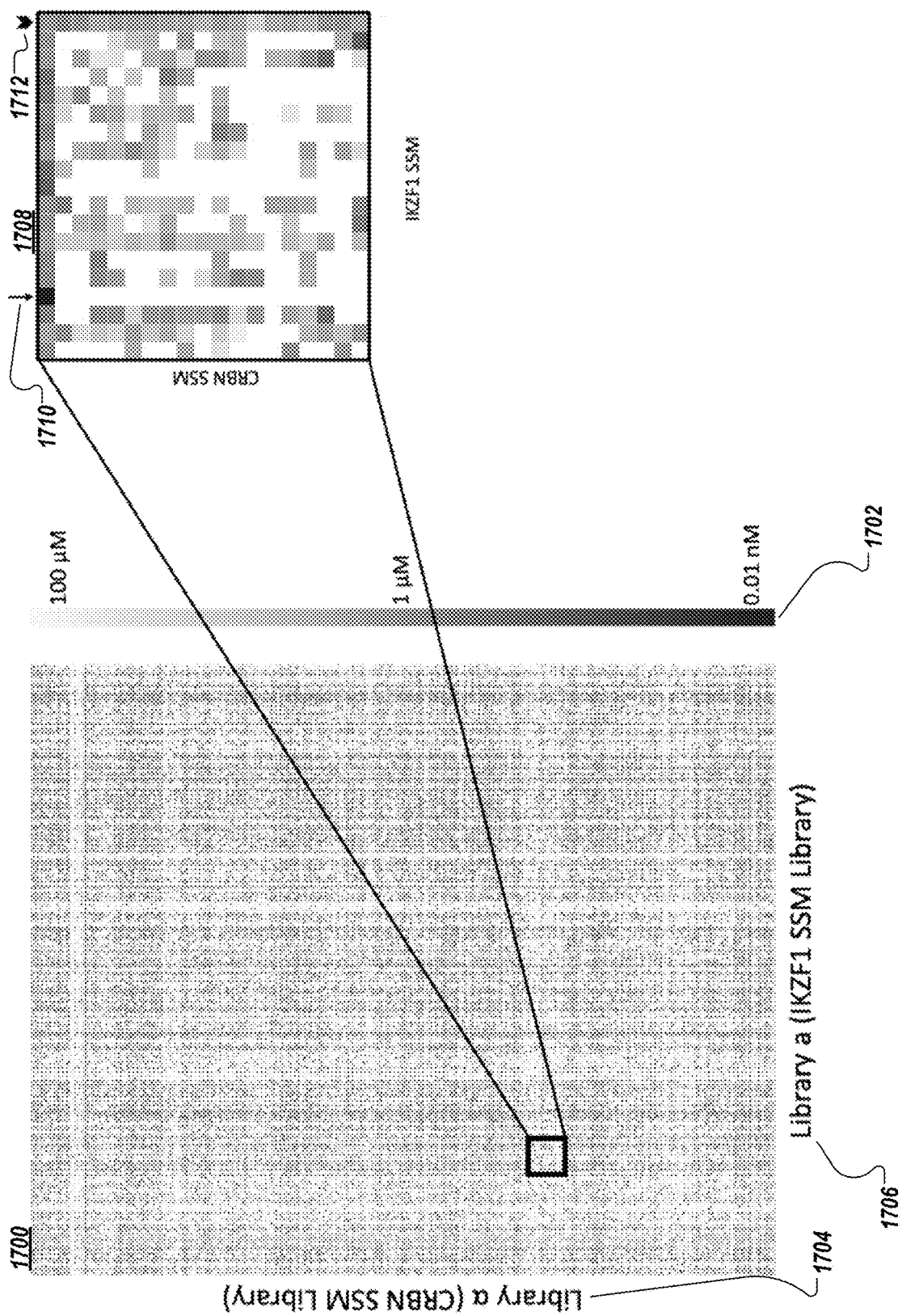
FIG. 17A illustrates a heatmap of quantitative binding affinity data representing intensities of interactions between a library of variants of the polypeptide E3 ubiquitin ligase cereblon (CRBN) and a library of variants of its polypeptide target substrate Ikaros (IKZF1).

FIG. 17A illustrates a heatmap 1700 of AlphaSeq data representing intensities of interactions between a library of variants of the polypeptide E3 ubiquitin ligase cereblon (CRBN) and a library of variants of its polypeptide target substrate Ikaros (IKZF1), wherein darker shading indicates a relatively stronger interaction between an individual CRBN variants and IKZF1 variant and lighter shading indicates a relatively weaker interaction, according to scale bar 1702. Individual members of the library of CRBN variants are represented by the vertical axis 1704 of the grid and individual members of the library of IKZF1 variants are represented by the horizontal axis 1706 of the grid. The shaded boxes of the heatmap represent the strength of the interaction between a single member of the library of polypeptide E3 ubiquitin ligases 1704 and a single member of the library of polypeptide target substrates 1706. The interaction of the wild-type E3 ubiquitin ligase CRBN and its wild-type target substrate IKZF1 is well-known in the art. The library of CRBN variants and the library of IKZF1 variants were each generated by site saturation mutagenesis. Heatmap 1708 depicts a subset of squares from heatmap 1700 zoomed in to highlight specific interactions in greater detail. The square indicated by arrowhead 1712 represents the interaction of wild-type CRBN and wild-type IKZF1 and the relatively light shading indicates a relatively modest binding affinity between the wild-type protein binding partners. The square indicated by arrow 1710 represents the interaction of wild-type CBRN with a mutant of IKZF1 that carries a mutation which introduces steric bulk to the interface between the two protein binding partners. The relatively dark shading indicates a binding affinity between wild-type CBRN and the mutant IKZF1 that is significantly higher than that of wild-type CBRN and wild-type IKZF1.

Figure 17B:
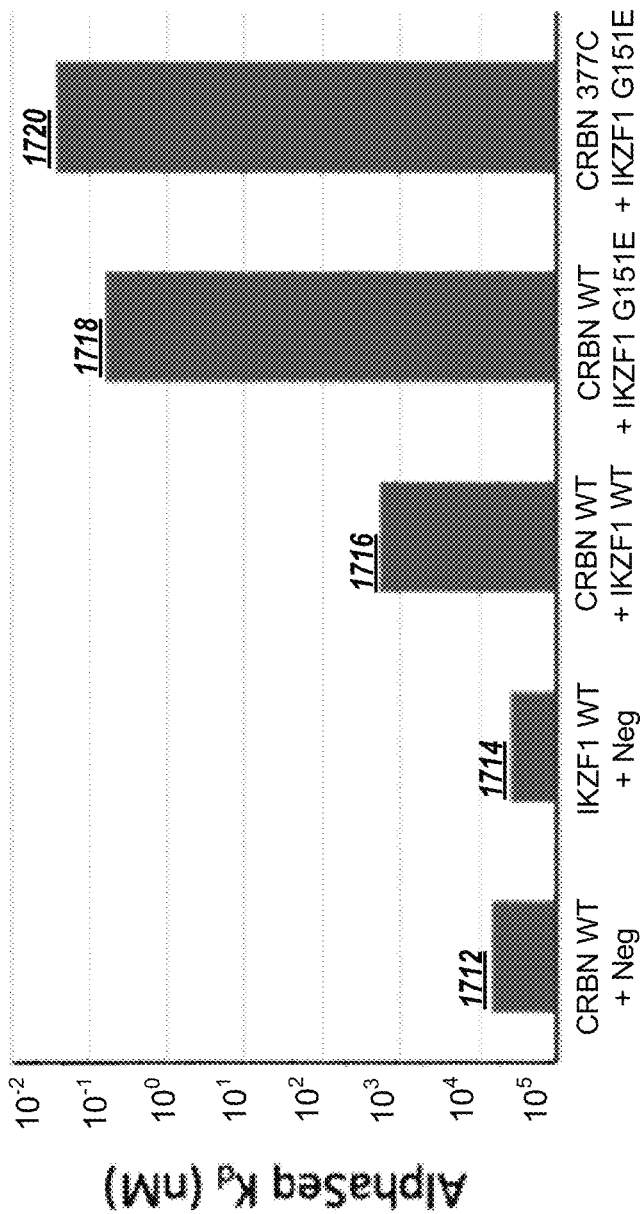
FIG. 17B is a plot of a subset of the binding affinity data represented in the heatmaps of FIG. 17A.

A subset of the binding affinity data represented in heatmaps 1700 and 1708 are represented in the plot of FIG. 17B. The interaction of wild-type CRBN and wild-type IKZF1 (1716) has a binding affinity at least one order of magnitude higher than that of wild-type CRBN (1712) and a negative control or wild-type IKZF1 and a negative control (1714). As indicated by heatmap 1708, the interaction of wild-type CRBN and a mutant of IKZF1, G151E which introduced steric bulk to the binding interface, increased binding affinity (1718) by at least three orders of magnitude relative to the binding affinity of wild-type CRBN and wild-type IKZF1 (1716). Further, the interaction of a mutant CRBN (E377C) and a mutant IKZF1 (G151E) increases binding affinity (1720) between the polypeptide E3 ubiquitin ligase and its target substrate even more significantly than for the interaction of wild-type CRBN and the mutant (G151E) IKZF1 (1718). These results demonstrate that the AlphaSeq assay robustly detects and quantifies the strength of interactions between polypeptide E3 ubiquitin ligases and polypeptide target substrates and shows that, combined with saturation mutagenesis libraries of protein binding partners, the assay may detect novel mutations which enhance the binding affinity between protein binding partners significantly relative to the binding affinity between wild-type protein binding partners. The novel mutations identified by the assay may then inform small molecule screening campaigns or rational drug design based on the predicted or observed impact of the mutation(s) on the binding interface between the protein binding partners.

Figure 18:
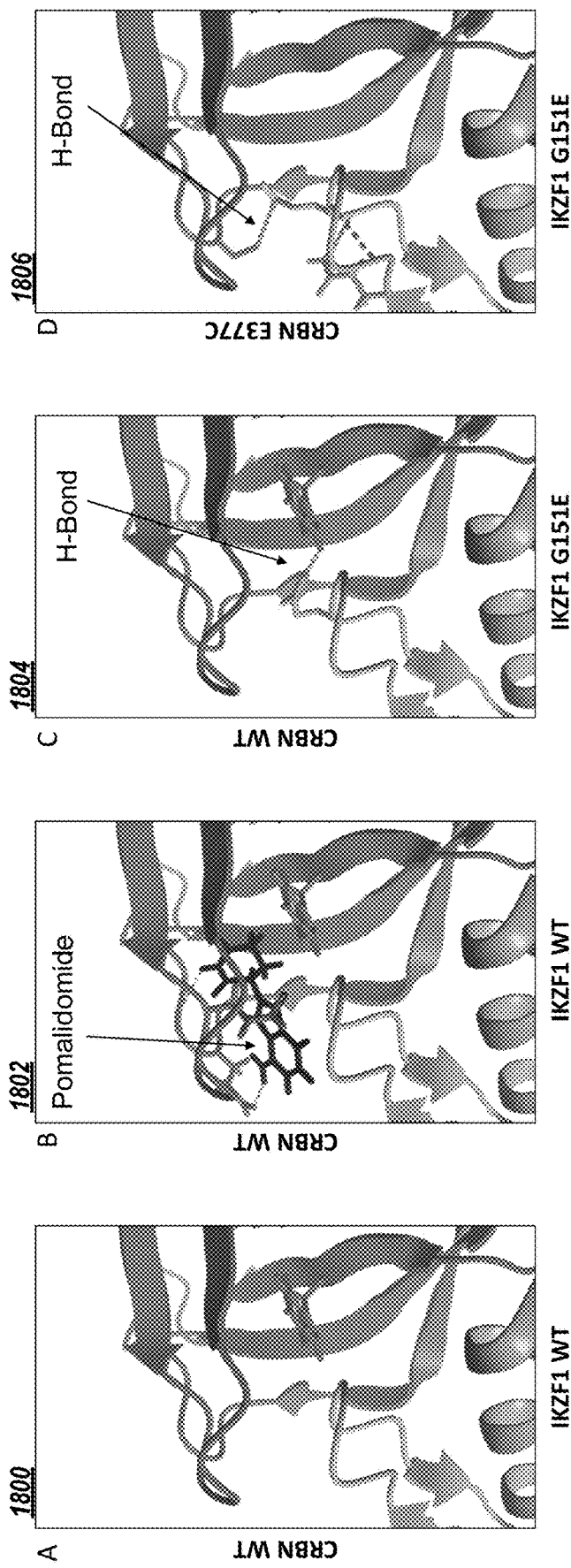
FIG. 18 illustrates structural models of the binding interface between CRBN and IKZF1, highlighting the binding interface of wild-type and mutant variants of CRBN and IKZF1.

FIG. 18 illustrates structural models of the binding between CRBN and IKZF1. The crystal structures of CRBN and IKZF1 are well-known, and the computation modeling program UCSF ChimeraX (Pettersen E F, Goddard T D, Huang C C, Meng E C, Couch G S, Croll T I, Morris J H, Ferrin T E. Protein Sci. 2021 January; 30(1):70-82.) was used to predict the impact of mutations identified in the experiment represented in FIGS. 17A and 17B. Panel 1800 depicts the predicted binding interface between wild-type CRBN and wild-type IKZF1. Panel 1802 depicts the predicted binding interface between wild-type CRBN and wild-type IKZF1 in the presence of the molecular glue pomalidomide. The immunomodulatory drug (IMiD) pomalidomide is well characterized in its role of enhancing the binding affinity between IKZF1 and CRBN, leading to the ubiquitination and degradation of IKZF1. Pomalidomide accomplished this by forming hydrogen bonds and stabilizing the interaction between CRBN and IKZF1 at the binding interface, as depicted in panel 1802. Panel 1804 depicts the predicted binding interface between wild-type CRBN and mutant (G151E) IKZF1, corresponding to the quantitative results plotted in FIG. 17B. Panel 1806 depicts the predicted binding interface between mutant CRBN (E377C) and mutant IKZF1 (G151E) corresponding to the quantitative results plotted in FIG. 17B. As highlighted by the arrows in panels 1804 and 1806, the mutations introduced to the protein binding partners also mediate hydrogen bonds between the protein binding partners and may stabilize the binding interface, leading to the enhanced binding affinity quantified in FIG. 17B. As shown in panel 1804, the IKZF1 mutation G151E is predicted to mediate a hydrogen bond between wild-type CRBN and mutant IKZF1. As shown in 1806, the IKZF1 mutation G151E and the CRBN mutation E377C are each predicated to mediate a hydrogen bond between mutant CRBN and mutant IKZF1. These results demonstrate the capabilities of the assay for detecting, in an unbiased screening method and without any prior knowledge of the binding interface, mutations which may stabilize the binding interactions between protein binding partners leading to a binding affinity that is substantially higher than the binding affinity between the wild-type protein binding partners. Combined with structural modeling and computational prediction, mutations identified by this method may be used to inform small molecule screening campaigns or rational drug design based on the predicted or observed impact of the mutation(s) on the binding interface between the protein binding partners.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A method comprising:
   a) expressing on the surface of haploid yeast cells in a first culture one or both of:
      i) one or more wild-type targeting proteins; and/or,
      ii) one or more modified targeting proteins with at least one amino acid difference from the wild-type targeting protein;
   b) expressing on the surface of haploid yeast cells in a second culture one or both of:
      i) one or more wild-type target proteins; and/or,
      ii) one or more modified target proteins with at least one amino acid difference from the wild-type target protein;
   c) combining the first culture of haploid yeast cells and second culture of haploid yeast cells in a single liquid culture such that the binding of a targeting protein with a target protein leads to the formation of diploid yeast cells; and,
   d) determining, based on the number of mating events between the haploid yeast cells of the first and second cultures, the amino acid sequence mutations of the targeting protein and/or target protein, or both the targeting protein and the target protein, that result in a dissociation constant between the targeting protein and the target protein of about ten-fold less than the interaction between the wild-type target protein and the wild-type targeting protein;
   wherein:
      the interaction between the wild-type target protein and the wild-type targeting protein has a dissociation constant (Kd) greater than about 100 nM; and,
      either the targeting protein or target protein is a ubiquitin ligase.

2. The method of claim 1 wherein one or more of the-modified target protein(s) and/or targeting protein(s) are truncated versions of their respective wild-type target or wild-type targeting protein.

3. The method of claim 1 wherein the one or more mutations are generated by targeted, random, or site saturation mutagenesis.

4. The method of claim 1 wherein the weak or strong interactions between the modified targeting protein and the target protein are determined to be any of about 20, 30, 40, 50, 100, 500, 1000 percent weaker or stronger than the interaction between the wild-type targeting and wild-type target proteins.

5. The method of claim 4 wherein the weak interaction has a dissociation constant (Kd) greater than about 1 um or 10 um.

6. The method of claim 4 wherein the strong interaction has a dissociation constant (Kd) less than about 10 nm or 1 nm.

7. The method of claim 4 wherein the difference between the weak interaction and one or more strong interactions is greater than or equal to any of 1, 2, or 3 orders of magnitude in Kd space.

8. The method of claim 1 wherein the ubiquitin ligase is an E3ubiquitin ligase.

9. The method of claim 1 wherein one or more of the mutations adds steric bulk to the targeting and/or target proteins.

10. The method of claim 4 further comprising determining a structure of an interface between two proteins composing the strong interaction.

11. The method of claim 10 wherein the structure is determined using crystallography.

12. The method of claim 10 wherein the structure is subsequently determined with computational modeling.

13. The method of claim 4 wherein the structure of the weak interaction is subsequently predicted by taking the structure of the strong interaction and computationally reverting all amino acids back to those found in the wild-type target protein and wild-type targeting protein.

14. The method of claim 10, further comprising identifying a small molecule compound that stabilizes the weak interaction.

15. The method of claim 1, further comprising using polynucleotide libraries to express the proteins on the surface of the haploid yeast cells, wherein the polynucleotide libraries encode up to about 10,000 targeting proteins and about up to about 10,000 target proteins.

16. The method of claim 1 wherein the first and second cultures of haploid yeast cells are Mat a and Mat α cells, respectively, incapable of mating according to any native sexual agglutination process.

17. The method of claim 1 wherein the number of mating events in the determining step is measured with next generation DNA sequencing.

18. The method of claim 10 wherein the ubiquitin ligase is an E3 ubiquitin ligase.

19. The method of claim 14 wherein the ubiquitin ligase is an E3 ubiquitin ligase.

20. The method of claim 15 wherein the ubiquitin ligase is an E3 ubiquitin ligase.

* * * * *